(12) United States Patent
Kim

(10) Patent No.: US 11,819,611 B1
(45) Date of Patent: Nov. 21, 2023

(54) SYSTEM AND METHOD FOR PRESSURE MANAGEMENT AND AIR LEAK DETECTION OF AN INFLATABLE CUFF IN A MEDICAL DEVICE

(71) Applicant: Kevin Chong Kim, Holmdel, NJ (US)

(72) Inventor: Kevin Chong Kim, Holmdel, NJ (US)

( * ) Notice: Subject to any disclaimer, the term of this patent is extended or adjusted under 35 U.S.C. 154(b) by 0 days.

(21) Appl. No.: 18/103,641

(22) Filed: Jan. 31, 2023

Related U.S. Application Data

(63) Continuation-in-part of application No. 17/902,691, filed on Sep. 2, 2022, which is a continuation-in-part
(Continued)

(51) Int. Cl.
*A61M 16/04* (2006.01)

(52) U.S. Cl.
CPC .... *A61M 16/0434* (2013.01); *A61M 16/0479* (2014.02); *A61M 16/0486* (2014.02); *A61M 16/0463* (2013.01)

(58) Field of Classification Search
CPC ............ A61M 16/0434; A61M 16/044; A61M 16/0443; A61M 16/0454; A61M 16/0456; A61M 16/0463; A61M 16/0475; A61M 16/0477; A61M 16/0479; A61M 16/0481; A61M 16/0484; A61M 16/0486; A61M 2205/15; A61M 2205/588
See application file for complete search history.

(56) References Cited

U.S. PATENT DOCUMENTS 3,481,339 A   12/1969  Puig
5,339,809 A   8/1994   Beck, Jr. et al.
(Continued)

FOREIGN PATENT DOCUMENTS

DE   202020101607 U1   4/2020
EP        2077865 B1   5/2012
(Continued)

OTHER PUBLICATIONS

PCT/U2023/025710. International Search Report & Written Opinion (dated Jul. 24, 2023).
(Continued)

*Primary Examiner* — Joseph D. Boecker
*Assistant Examiner* — Brian T Khong
(74) *Attorney, Agent, or Firm* — LOZA & LOZA, LLP; Jessica W. Smith

(57) ABSTRACT

An endotracheal or tracheostomy tube with a cuff assembly includes a cuff pressure regulator and a leak detection system. Pressure sensors monitor and measure a tracheal wall pressure and pressures in the cuff assembly. An abnormal reading from the pressure sensors may initiate a cuff-pressure adjusting process. The leak detection system detects an air leak in the seal between the cuff assembly and the tracheal wall. A scented film with a predetermined scent is positioned on an inferior portion of the cuff assembly, distally from the seal with the tracheal wall. An air leak is indicated when the predetermined scent is detected in air in the trachea proximal to the cuff assembly. An air-circulation device generates air flow into the trachea such that a new batch of air may be sampled and tested. The detection of an air leak may initiate a cuff-pressure adjusting process.

21 Claims, 13 Drawing Sheets

Related U.S. Application Data of application No. 17/848,273, filed on Jun. 23, 2022, now Pat. No. 11,602,605.

(56) References Cited

U.S. PATENT DOCUMENTS

| | | |
|---|---|---|
| 9,132,212 B2 | 9/2015 | Clayton |
| 9,709,540 B2 | 7/2017 | Lee et al. |
| 10,369,312 B2 | 8/2019 | Pendleton et al. |
| 2003/0041863 A1 | 3/2003 | Hargis |
| 2004/0255951 A1* | 12/2004 | Grey .................... A61M 16/04 128/207.14 |
| 2007/0068517 A1* | 3/2007 | Crohn .................. A61M 16/04 128/200.24 |
| 2008/0078403 A1 | 4/2008 | Clayton |
| 2010/0288289 A1 | 11/2010 | Nasir |
| 2012/0279500 A1 | 11/2012 | Singvogel et al. |
| 2015/0101598 A1 | 4/2015 | Wang |
| 2015/0367093 A1 | 12/2015 | Clayton |
| 2016/0228662 A1 | 8/2016 | Pendleton et al. |
| 2017/0340216 A1 | 11/2017 | Morgan et al. |
| 2019/0090594 A1 | 3/2019 | Ong |
| 2021/0402120 A1 | 12/2021 | Tupper et al. |
| 2022/0080141 A1 | 3/2022 | Göbel |
| 2022/0152330 A1* | 5/2022 | Cameron .......... A61M 16/0434 |

FOREIGN PATENT DOCUMENTS

| | | |
|---|---|---|
| WO | 9966975 A1 | 12/1999 |
| WO | 2011127407 A1 | 10/2011 |
| WO | 2016209192 A2 | 12/2016 |

OTHER PUBLICATIONS

PCT/U2023/025707. International Search Report & Written Opinion (dated Jul. 26, 2023).

PCT/U2023/012533. International Search Report & Written Opinion (dated May 10, 2023).

* cited by examiner

SYSTEM AND METHOD FOR PRESSURE MANAGEMENT AND AIR LEAK DETECTION OF AN INFLATABLE CUFF IN A MEDICAL DEVICE

CROSS REFERENCE TO RELATED APPLICATIONS

This application is a continuation-in-part application under 35 U.S.C. § 120 of currently pending application Ser. No. 17/902,691 filed Sep. 2, 2022, which is incorporated by reference in its entirety herein, which claims priority as a continuation-in-part application under 35 U.S.C. § 120 of currently pending application Ser. No. 17/848,273, filed Jun. 23, 2022, which is incorporated by reference in its entirety herein.

FIELD

This application relates to system and methods for a tracheostomy and/or endotracheal tube and more particularly to a pressure management and air leak detection system and method for an inflatable cuff assembly implemented on the endotracheal tube and/or tracheostomy tube.

BACKGROUND

Mechanical ventilation (MV) is a life supporting measure whereby a patient is intubated with a breathing tube and receives oxygen and air delivered by a machine through the breathing tube. A mechanically ventilated patient experiences a physiologically altered milieu: reduced ability to clear oral and nasal secretions, diminished tracheobronchial mucociliary clearance, increased accumulation of secretions in the lungs and bronchus, reduced cough reflex, and increased likelihood of gastric reflux. The combined effect of these factors is to predispose a mechanically ventilated patient to ventilator-associated pneumonia (YAP), an infection of the lungs that develops typically after 48 hours of being on mechanical ventilation.

The breathing tube in mechanical ventilation includes an endotracheal tube (ETT) or tracheostomy tube including an inflatable cuff. The inflatable cuff provides a seal between the breathing tube and the wall of the trachea to help prevent seepage of secretions into the lungs and bronchus. An accumulation of secretions above the inflatable cuff in ventilated patients is a normal physiological phenomenon. The sources of secretions are oral cavity, sinuses, and stomach (the "orogastric secretions"). It is known that under normal conditions, the oral cavity and sinuses produce up to 3 liters of secretions per day. Again, these oral cavity and sinus secretions do not include gastric refluxate, which may also be significant. While a healthy person can eliminate and/or manage such secretions, a ventilated patient cannot. Instead, in a ventilated patient, secretions may accumulate above the inflatable cuff and/or leak around the inflatable cuff into the trachea.

The concern with accumulation of secretions above the cuff is that secretions are loaded with microorganisms including bacteria and fungus. Since the secretions are heavily contaminated, they should be kept away from sterile organs of the human body. The lungs are one of those sterile organs. As such, it becomes imperative for a treating physician to do the utmost to keep the secretions out of the patient's lungs.

The inflatable cuff can be a powerful aspiration-deterrent mechanism. The inflatable cuff, located at the distal end of a breathing tube, when inflated, is supposed to contact the tracheal wall circumferentially resulting in a complete seal. The inflatable cuff, unfortunately, is known to not provide an efficient seal principally due to the formation of wrinkles or folds from the over-sized cuff as discussed below. This observation substantiates a study that showed that about 10% of patients on mechanical ventilation develop ventilator-associated pneumonia (VAP), and the mortality rate in VAP is estimated at 13%. In addition, patients with VAP face a longer hospital course and incur higher healthcare costs than similarly ill patients without VAP. Given that in the U.S., there are approximately 750,000 patients annually that require ventilation, the human and financial tolls of VAP is enormous.

Maintenance of the cuff pressure within the recommended range is recognized as a critical component of patient care, vis-a-vis reduction of tracheal injury and prevention of ventilator-associated pneumonia. The ultimate purpose of monitoring the cuff pressures is to achieve a sufficiently high pressure that maintains a good seal between the trachea and the cuff to prevent leakage of secretions, but a low enough pressure to avoid compromising tracheal blood flow.

Today, several cuff pressure management systems are on the market. The cuff pressure management systems, however, fail to show clinically significant benefits vis-a-vis the incidence of ventilator-associated pneumonia (VAP) and patient outcome measures. Thus, there is a need for improved cuff pressure management systems and methods to help reduce the incidence of VAP and improve patient outcomes.

SUMMARY

In one aspect, a medical device includes an airway tube configured for implantation within a trachea and a cuff assembly implemented on a distal portion of the airway tube, wherein the cuff assembly includes at least one inflatable cuff. At least one scented material is positioned on a distal side of the cuff assembly or on a portion of the airway tube distal from the cuff assembly. At least one scent detector is configured to detect a predetermined scent from the scented material in air, wherein the air is sampled from the trachea on a proximal side of the cuff assembly.

In another aspect, a medical system includes an airway tube configured for implantation within a trachea and a cuff assembly on a distal portion of the airway tube. The medical system further includes at least one scented material positioned on a distal side of the cuff assembly or on a portion of the airway tube distal from the cuff assembly, wherein the at least one scented material includes at least one predetermined scent. An air intake opening is formed in an outer wall of the airway tube proximally from the cuff assembly, and a suction channel extends from the air intake opening to a proximal end of the airway tube.

In another aspect, a medical system includes an airway tube configured for implantation within a trachea and a cuff assembly on a distal portion of the airway tube, wherein the cuff assembly includes an inner cuff positioned adjacent to the airway tube and an outer bladder positioned adjacent to the inner cuff. At least one scented material is positioned on an inferior aspect of the inner cuff or on a portion of the airway tube distal from the cuff assembly, wherein the at least one scented material includes at least one predetermined scent. At least one scent detector is configured to detect the at least one predetermined scent in supracuff air from the trachea.

In one or more of the above aspects, the airway tube includes an air intake opening formed in an outer wall of the airway tube proximally from the cuff assembly and a suction channel extending from the air intake opening to a proximal end of the airway tube.

In one or more of the above aspects, a vacuum pump is fluidly coupled to the suction channel at the proximal end of the airway tube, wherein the vacuum pump suctions the air from the trachea through the air intake opening and suction channel. A filter may be used to remove fluids from the air prior to testing by the at least one scent detector.

In one or more of the above aspects, a pressure regulator system is configured to adjust a pressure in the at least one inflatable cuff of the cuff assembly in response to the scent detector.

In one or more of the above aspects, a pressure regulator is configured to determine the scent detector has detected a leak in the seal around the cuff assembly and generate an alert on a user interface, wherein the alert includes one or more of: an audible alert or a visual alert. The pressure regulator is also configured to adjust the pressure in the at least one inflatable cuff of the cuff assembly in response to the detected leak.

In one or more of the above aspects, a first inflation lumen includes a first distal end coupled to an interior of the at least one inflatable cuff. The first inflation lumen also includes a second proximal end fluidly coupled to a first air pump and a first release valve to add or remove air from the at least one inflatable cuff.

In one or more of the above aspects, a pressure sensor device measures a tracheal wall pressure exerted by the cuff assembly.

In one or more of the above aspects, the pressure regulator adjusts the pressure in the at least one inflatable cuff of the cuff assembly in response to the detected leak and the tracheal wall pressure.

In one or more of the above aspects, the at least one inflatable cuff is an inner cuff positioned adjacent to the airway tube, and the cuff assembly further includes an inflatable outer bladder positioned adjacent to an outer surface of the inner cuff.

In one or more of the above aspects, the pressure sensor device that is configured to measure the tracheal wall pressure is positioned between the inner cuff and the outer bladder.

In one or more of the above aspects, the inner cuff is inflated within a first pressure range and the outer bladder is configured to be inflated within a second pressure range, wherein the first pressure range is less than the second pressure range.

In one or more of the above aspects, the at least one scented material comprises a scent-embedded polymer film, wherein the scent-embedded film is not degradable, is water resistant, and does not alter an elasticity of the at least one inflatable cuff.

In one or more of the above aspects, the predetermined scent in the at least one inflatable cuff is released in detectable amounts over a period between two to three months.

In one or more of the above aspects, the at least one scent detector is configured for detection of the at least one predetermined scent in supracuff air from the trachea.

In one or more of the above aspects, a user interface emits an audible or visible alert when the at least one scent detector detects the at least one predetermined scent in the supracuff air.

In one or more of the above aspects, a pressure regulator is configured to adjust a pressure of the cuff assembly when the at least one scent detector detects the at least one predetermined scent in the supracuff air.

In one or more of the above aspects, a pressure sensor device measures a tracheal wall pressure exerted by the cuff assembly. The pressure regulator adjusts the pressure of the cuff assembly in response to the tracheal wall pressure.

In one or more of the above aspects, a pressure regulator adjusts a pressure of the inner cuff and/or the outer bladder in response to the scent detector detecting the at least one predetermined scent.

DETAILED DESCRIPTION

Figure 1:
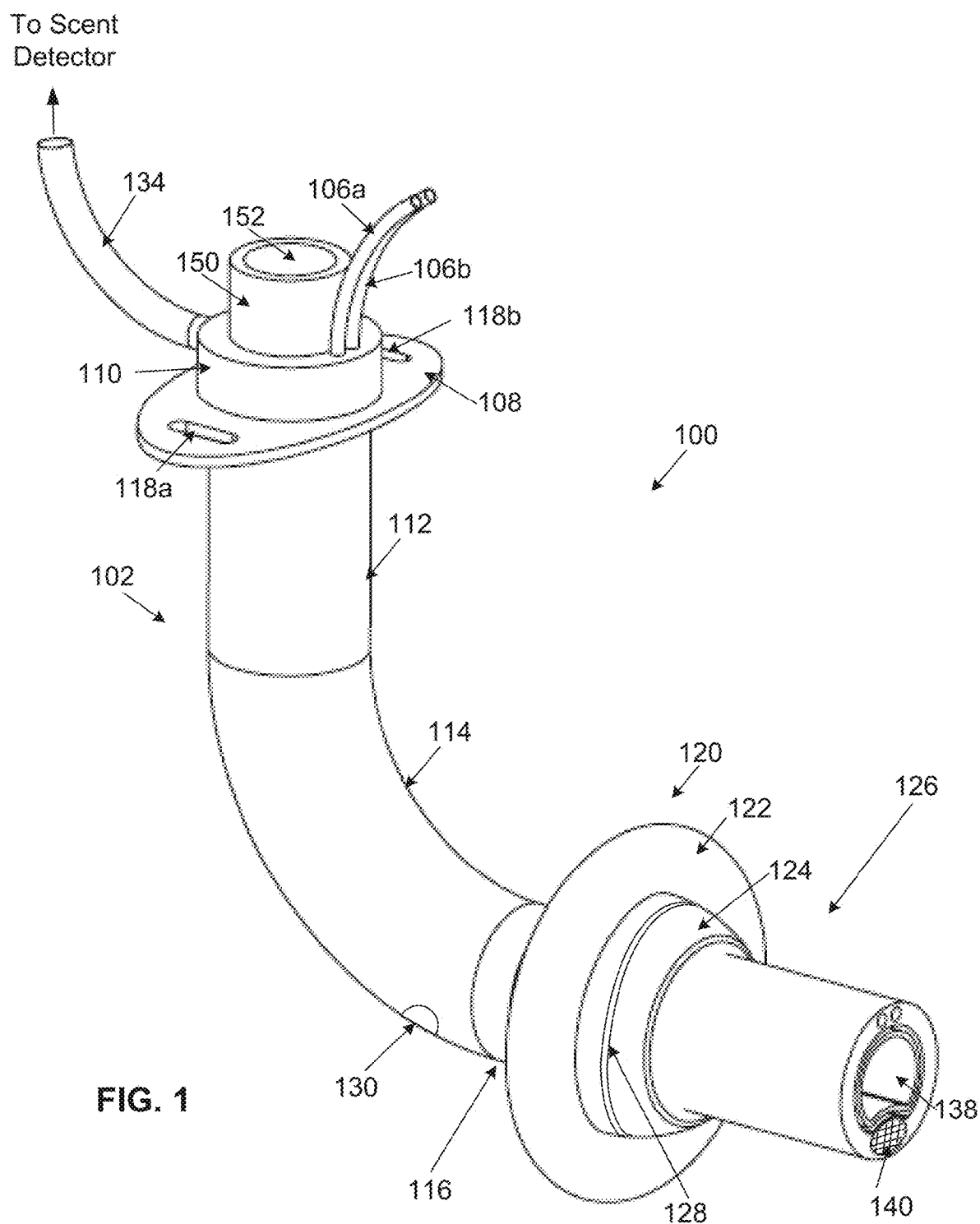
FIG. 1 illustrates a perspective view of an embodiment of an airway tube with leak detection.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Current pressure management systems require manually monitoring and regulating cuff pressures for an endotracheal tube or tracheostomy tube. This manual regulation is impractical and unreliable and takes valuable time away from the hospital staff. The present application describes a new and innovative pressure management system that continuously receives and processes input from relevant sources, and seamlessly, and automatically adjusts the pressure in the inflatable cuffs. Such an automatic system reduces the work of the hospital staff and helps to protect the patients from tracheal injuries and ventilator-associated pneumonia.

In addition, current pressure management systems tend to fail due to their inability to detect leaks around the inflatable cuff. For, ultimately, whether a patient will experience VAP depends on the spillage of oronasal secretions into the lungs, which hinges on the existence of a gap between the cuff and the tracheal wall. The existence of a gap between the cuff and tracheal wall may be detected by measuring an air leak in the seal. The present application describes a new and innovative pressure management system and methods that can accurately determine an air leak in the seal formed by an inflatable cuff against the tracheal wall.

Another crucial reason for the failure of current pressure management systems is due to their inability to accurately determine the pressure that the cuff is exerting on the tracheal wall (the tracheal wall pressure). The current pressure management systems only measure the pressure within the cuff (intracuff pressure). But the intracuff pressure reveals little about the tracheal wall pressure. The level of safety of the cuff inflation level is proportional to the tracheal wall pressure, and not the intracuff pressure. Caring for intubated patients without knowing this vital information is less than ideal. The current practice of adjusting the cuff pressure based on an arbitrary target level (CDC recommended level of 25 cm $H_2O$) represents a total disregard for what is essential for the patient's safety and well-being. The present application further describes a new and innovative pressure management system and methods that accurately determine the tracheal wall pressure and improve patient outcomes.

Overview

A pressure management system is described herein having an effective means to monitor a tracheal wall pressure by utilizing an intercuff pressure sensor affixed at an interface between an inner cuff and an outer bladder of a dual cuff assembly. The pressure management system performs pressure checks at predetermined intervals and adjusts a cuff volume to achieve a predetermined pressure in the cuff assembly. A leak detection system is also described herein that detects an air leak in the seal between the tracheal wall and the cuff assembly. A strip of scent-impregnated plastic film or other material is affixed to an inferior portion of the cuff assembly below the seal with the tracheal wall. In this configuration, an air leak in the seal causes the scent from the plastic film to escape and flow into the air of the trachea proximal to the cuff assembly. A scent detector is configured to sample the air proximal to the cuff assembly. When the scent detector detects the scent, an alert is generated. The pressure management system receives input from scent detector as well as the pressure sensors. The pressure management system automatically adjusts a pressure in the cuff assembly and generates alerts in response to the inputs from the pressure sensors and the scent detector.

Embodiments of an Airway Tube with a Dual Cuff Assembly

An airway tube including a tracheostomy tube or an endotracheal tube or other medical tube with an inflatable cuff assembly is now described in more detail. In one embodiment, the inflatable cuff assembly includes dual cuffs. Unlike previously known inflatable cuffs, the dual cuff assembly described herein comprises at least two separately controlled inflatable cuffs. Currently, there are two main types of cuffs, low volume, high pressure (LVHP) cuffs and high volume, low pressure (HVLP) cuffs. The first type, LVHP cuffs, are made from stiffer, relatively inelastic materials. Due to their inherent stiffness, a greater level of pressure (50 cm $H_2O$ to 100 cm $H_2O$) is required to inflate LVHP cuffs. As a result, LVHP cuffs cause an excessively high pressure on the tracheal mucosa, even when inflated to a minimum pressure to create a seal with the tracheal wall. This high pressure causes an unacceptably high incidence of tracheal ischemia and necrosis, e.g., a 5%-20% incidence rate. Despite that, one crucial advantage of LVHP cuffs, when inflated, is the relative absence of folds or wrinkles, resulting in superior tracheal sealing. LVHP cuffs were first employed in the 1960's, but, today, have been widely replaced by HVLP cuffs.

HVLP cuffs are composed of more elastic, compliant materials that inflate at lower pressures. To compensate for the lower pressure characteristics and create a seal against the tracheal wall, the diameter of the HVLP cuffs are generally 1.5-2 times the diameter of the trachea when fully inflated. However, the increased volume of the HVLP cuffs requires a significant amount of cuff material that adds bulkiness to the HVLP cuff making it more difficult to intubate. Moreover, the excess material has a tendency to form wrinkles or folds due to "incomplete inflation." These wrinkles or folds often create paths for orogastric secretions to pass beyond the HVLP cuff, ultimately leading to microaspiration and infection of the lungs.

In examining the effect of cuff pressure on the trachea, it is important to keep in mind that the tracheal wall mucosa capillary perfusion pressure in humans ranges from 22 to 32 mmHg, and tracheal mucosal blood flow may be compromised at applied pressures above 30 cm $H_2O$ (22 mmHg), with total occlusion of flow to certain parts at 50 cm $H_2O$ (37 mmHg). It is apparent, then, that there is only a small overlap between the safety pressure range and that of complication. The window of efficacy and safety, indeed, is very narrow, if nonexistent.

The required pressure for typical HVLP cuffs to achieve a reasonable inflation with an acceptable number of folds or wrinkles is about 32 cm $H_2O$. The guidelines established by various medical societies and organizations recommend maintaining the HVLP cuff pressure within a range of 20 cm $H_2O$ to 30 cm $H_2O$ to avoid occlusion of tracheal mucosal blood flow. Unfortunately, studies have shown that even at pressures up to 60 cm $H_2O$, microaspiration still occurs with HVLP cuffs, suggesting the continued presence of cuff wrinkles, allowing the passage of secretions, even at higher pressures. So, even though HVLP cuffs appear superior because they are capable of producing a seal at a lower pressure level and avoiding necrosis of the tracheal wall, they are still far from being ideal.

While the principal goals of the inflatable cuff, to provide a maximum airway seal and cause minimal damage to the airway, is simple and straightforward, successfully achieving these goals has been elusive. This failure continues despite the diverse modifications and advances that have been made vis-a-vis materials, shape, and volumetric structure. Thus, there is a need for an improved cuff system that helps to reduce microaspiration and infection of the lungs by maintaining a good seal with the tracheal wall but without unduly harming the tracheal wall.

In an embodiment described herein, a high-pressure outer bladder is attached to the outer surface of an inner cuff. The inner cuff couples to a distal end of an endotracheal tube or tracheostomy tube. The inner cuff is a low-pressure inflatable cuff and is configured to function at a low pressure range of 10 cm $H_2O$ to 20 cm $H_2O$. In contrast, the outer inflating bladder is configured to inflate to a high pressure range of 50 cm $H_2O$ to 150 cm $H_2O$. The inner cuff thus operates in a pressure range that is less than the pressure range of the outer bladder.

Figure 2:
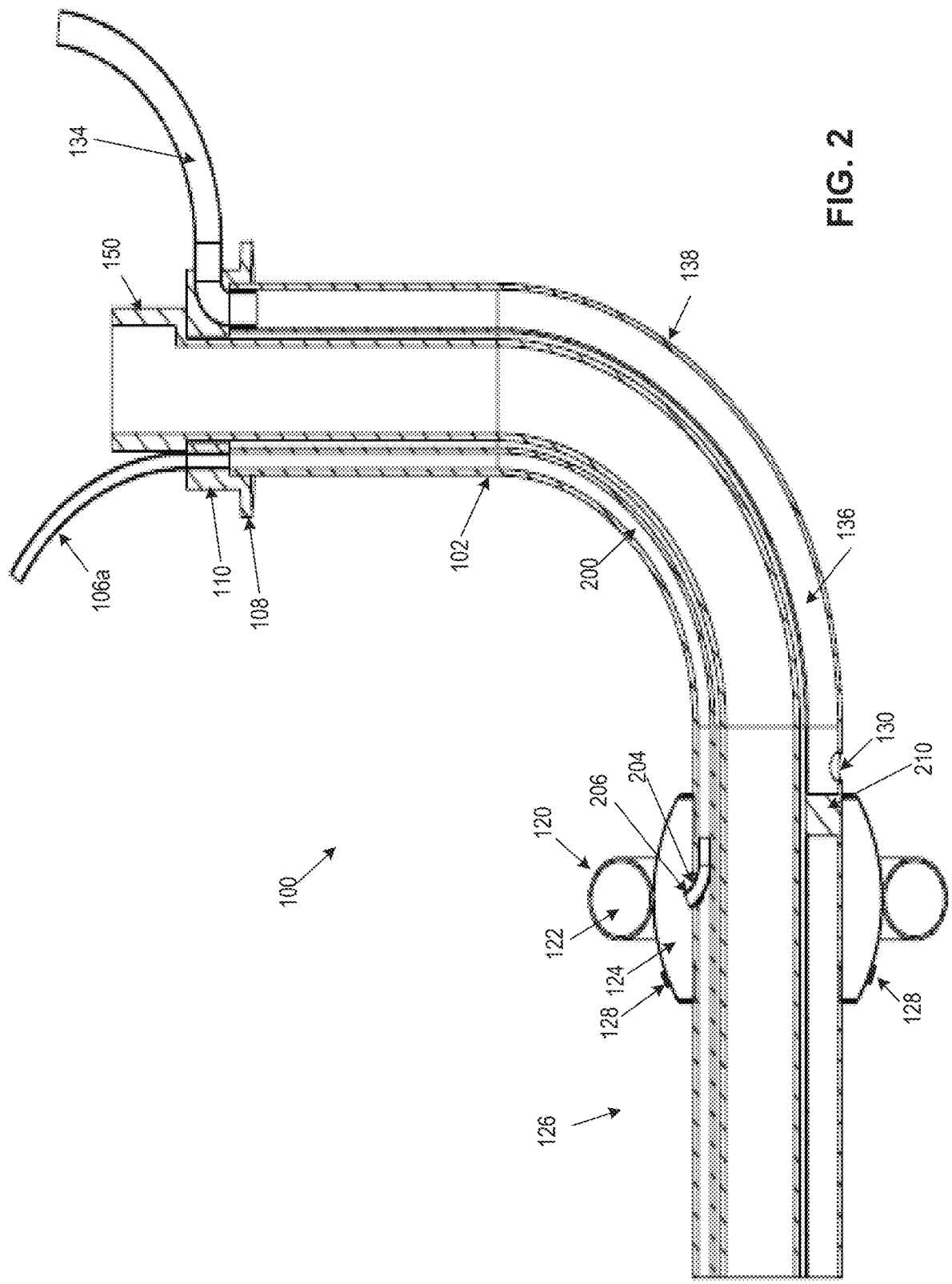
FIG. 2 illustrates a cross-sectional view of an embodiment of the airway tube with leak detection.
Figure 3:
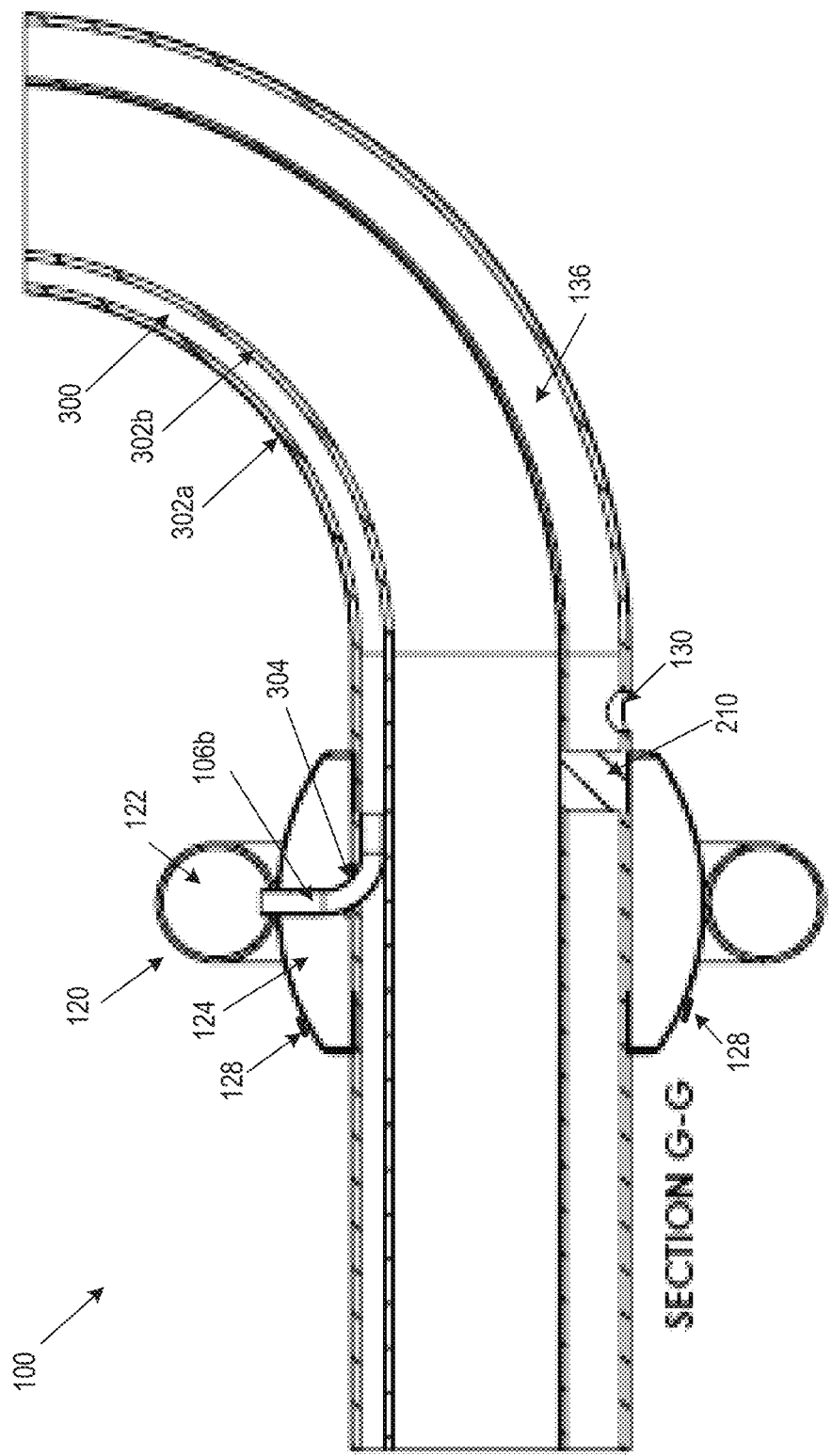
FIG. 3 illustrates another cross-sectional view of an exemplary embodiment of the airway tube with leak detection.

FIGS. 1-3 illustrate one embodiment of a tracheostomy tube 100 with leak detection. FIG. 1 illustrates a perspective view of the tracheostomy tube 100 and FIGS. 2-3 illustrate different cross-sectional views of the tracheostomy tube 100 shown in FIG. 1. Though a tracheostomy tube 100 is illustrated in this example, the leak detection system and method described herein may be implemented with an endotracheal tube or other medical device with an inflatable cuff or other type of airtight seal. The tracheostomy tube 100 in this example includes an outer cannula 102 and an inner cannula 150, wherein the inner cannula 150 is positioned internally to the outer cannula 102. The outer cannula 102 and the inner cannula 150 may comprise a soft polyvinyl chloride (PVC) material.

The outer cannula 102 includes a proximal segment 112, a curved middle segment 114, and a distal segment 116. The proximal segment 112 of the outer cannula 102 includes a flange 108 or plate that circumferentially extends outward and includes two slits 118a, 118b on opposing sides. A cotton bandage or strap is secured in the slits 118a, 118b of the flange 108 to hold the tracheostomy tube 100 against a neck of a patient. The proximal segment 112 further includes a hub 110 extending upward proximally from the flange 108. The inner cannula 150 is inserted through a proximal opening in the hub 110. The proximal opening 152 of the inner cannula 150 is configured for connection to a ventilator through a tube or hosing.

The outer cannula 102 of the tracheostomy tube 100 includes a curved middle segment 114 and a distal segment 116 configured and sized for implantation within a trachea of a patient. The middle segment 114 is curved such that the proximal segment 112 is between an approximately 80 degree to an approximately 90 degree angle to the distal segment 116. The distal segment 116 includes a cuff assembly 120, a distal end 126, and a main distal opening 138.

The tracheostomy tube 100 includes the novel dual cuff assembly 120 disposed at the distal segment 116. The cuff assembly 120 comprises at least two separately controlled inflatable cuffs, a first inner cuff and a second outer bladder 122. The first inner cuff 124 is positioned around and adjacent to the outer cannula 102 and is configured to inflate radially outwards from the tracheostomy tube 100. The second outer bladder 122 is positioned around and adjacent to an outer surface of the inner cuff 124 such that at least a portion of the inner cuff 124 lays between the outer bladder 122 and the tracheostomy tube 100. The outer bladder 122 is configured to inflate radially outward from the inner cuff 124 such that when implanted in a trachea of a patient, an outer surface of the outer bladder 122 contacts the tracheal wall and forms a seal.

The inner cuff 124 and the outer bladder 122 may be a cylindrical or toroidal shape. For example, as seen in FIG. 1, the outer bladder 122 is a torus shaped ring with a circular cross section when inflated. The inner cuff 124 has a cylindrical shape with an arched outer surface that forms a ring around the tracheostomy tube 100. In this example, the length of the inner cuff is in the range of 10 mm to 20 mm, and the length of the outer cuff is in the range of 5 mm to 9 mm. The outer bladder 122 is bonded to the inner cuff 124 and not tethered to the outer cannula 102 of the tracheostomy tube 100. The inner cuff 124 is attached to the outer cannula 102 by an adhesive and/or a band. These specifications are exemplary and the inner cuff 124 and/or the outer bladder 122 may have alternate shapes, dimensions and attachment means.

The inner cuff 124 and the outer bladder 122 are configured for differing operating pressures, and so the tracheostomy tube 100 includes a means to inflate the inner cuff 124 and the outer bladder 122 to different pressures. In one example, a first inflation line 106a is positioned in a first channel 200 shown in FIG. 2. The first channel 200 is formed between an inner wall and an outer wall of the outer cannula 102. The first channel 200 extends from a proximal side of the flange 108, such as at the hub 110, to at least the cuff assembly 120 on an anterior side of the outer cannula 102. A distal end 206 of the inflation line 106a extends through an opening 204 in the outer wall of the outer cannula 102 and into the inner cuff 124. The inflation line 106a forms an airtight, fluid connection for inflation and deflation of the inner cuff 124.

A second inflation line 106b is positioned in a second channel 300 shown in FIG. 3. The second channel 300 is formed between an inner wall 302b and an outer wall 302a on an anterior side of the outer cannula 102. The second channel 300 extends from a proximal side of the flange 108 at the hub 110 of the outer cannula 102 to at least the cuff assembly 120. The second inflation line 106b is positioned inside the second channel 300. A distal end of the inflation line 106b extends through a sealed opening 304 in the outer wall 302a of the outer cannula 102 into the outer bladder 122. The inflation line 106b thus forms an airtight, fluid connection for inflation and deflation of the outer bladder 122.

In this embodiment, there are two channels 200, 300 formed in the anterior wall of the outer cannula 102 for holding the inflation lines 106a, 106b. In another embodiment, the two channels 200, 300 may be formed in a lateral wall of the outer cannula 102. In yet another embodiment, a single channel may hold both inflation lines 106a, 106b. In yet another embodiment, the channels 200, 300 may be formed between the inner cannula 150 and outer cannula 102, e.g. on the anterior side of the tracheostomy tube 100. Other implementations may also be possible for positioning the inflation lines 106a, 106b from a proximal side of the flange 108 to the cuff assembly 120 of the tracheostomy tube 100.

Due to the separate means for inflation, such as inflation lines 106a-b, the outer bladder 122 and inner cuff 124 may be inflated to and maintained at different pressures. In an embodiment, the inner cuff 124 is a low-pressure inflatable cuff and is configured to function at a low pressure range of 10 cm $H_2O$ to 20 cm $H_2O$. In contrast, the outer inflating bladder 122 is configured to inflate to a higher pressure range of 50 cm $H_2O$ to 150 cm $H_2O$. The inner cuff 124 thus operates in a pressure range that is less than the pressure range of the outer bladder 122.

In addition, the inner cuff 124 comprises a relatively elastic material while the outer bladder 122 comprises a relatively inelastic material, e.g., the material of the outer bladder 122 is less elastic than the material of the inner cuff 124. For example, the relatively elastic material of the inner cuff 124 may include one or more of: rubber, silicone, latex, polyvinyl chloride (PVC), neoprene, polyisoprene, or polyurethane (PU). The relatively inelastic material of the outer bladder 122 may include one or more of: polyethylene teraphthalate (PETP), low-density polyethylene (LDPE), polyvinyl chloride (PVC), silicone, neoprene, polyisoprene, or polyurethane (PU).

In use, e.g., when positioned into a trachea of a patient and pressurized to an inflated state, the first, inner cuff 124 behaves as a HVLP type cuff while the second, outer bladder 122 behaves as a LVHP type cuff. The more compliant inner cuff 124 is able to temper the pressure applied on the tracheal wall (the "tracheal pressure") by the higher pressurized outer bladder 122. In other words, the lower pressure, more elastic inner cuff 124 is configured to absorb excessive pressure that may otherwise be exerted on the tracheal wall by the outer bladder 122. For example, since the inner cuff 124 is more compliant and elastic, the cuff assembly 120 applies a lower total pressure/force against the tracheal wall, e.g., lower than the outer bladder pressure. The force of the inner cuff 124 acts radially on the outer bladder 122 and thus represents the force ultimately exerted on the trachea as the tracheal pressure. So, the radial force produced by the inner cuff 124 and acted upon the outer bladder 122, then, is the tracheal pressure. For example, when the outer bladder pressure is greater than that of the inner cuff pressure, and the outer bladder 122 is inflated so that the outer surface touches the trachea, the intercuff pressure is the same as the tracheal wall pressure.

In addition, due to its operation at a high pressure, the outer bladder 122 in an inflated state forms a relatively smooth surface with fewer folds or wrinkles, e.g. than a LVHP cuff. This reduction in wrinkles reduces the risk for leakage and creates a more uniform tracheal seal.

In this way, the cuff assembly 120 utilizes an innovative system to titrate the tracheal pressure thereby reducing tracheal complications. By incorporating the characteristics of HVLP and LVHP cuffs into the cuff assembly 120, the cuff assembly 120 exploits the advantages found in both types of cuffs: superior tracheal seal and greater safety to the trachea. The cuff system 120 features the advantages of superior seal against the tracheal wall with reduced tracheal damage. The cuff assembly 120 thus helps protect the lungs from being contaminated with orogastric contents or blood without undue harm to the tracheal wall.

The cross-section of the airway tube 100 in FIG. 2 further shows the suction channel 136 and tubing 134 coupled thereto. The air intake opening 130 is shown on a posterior side of the airway tube but may be positioned anteriorly or otherwise on a proximal side of the cuff assembly 120. In this example, a stopper 210 is positioned in the suction channel 136 distally from the air intake opening 130. The stopper 210 is sized to block and provide a seal to the suction channel 136 to prevent air or fluids from flowing to the distal end 126 of the airway tube 100.

Embodiment of the Leak Detection System

In an embodiment, the tracheostomy tube 100 also includes a leak detection system that detects an air leak in the seal between the tracheal wall and the cuff assembly 120. The leak detection system includes a scent-impregnated plastic film 128 or other material, as shown in FIGS. 1-3, positioned on a distal end 126 of the tracheostomy tube 100, e.g., distally to the seal with the tracheal wall. In this example, the scented film 128 includes a strip affixed circumferentially around an anterior portion of the inner cuff 124.

The scented film 128 may include one or more types of scents—woody scents, fresh scents, herbaceous scents, floral scents, fruity scents, etc. The predetermined scent is preferably long-lasting, well-tolerated, pleasing, and safe for humans. The predetermined scent, furthermore, is configured to interact chemically with a chemical sensor of a scent detector.

The one or more predetermined scents are impregnated into one or more plastic polymers and manufactured into thin films. The one or more plastic polymers may include polyethylene, polypropylene, polystyrene, cellulose derivatives, and acrylonitrilbutadiene-styrene. The one or more plastic polymers are formulated such that the impregnated scents are released slowly in detectable amounts over a long period, such as 2 to 3 months after opening. The thin films preferably have a long shelf-life, e.g. such as with a sealed, airtight packaging, that preserves the one or more predetermined scents impregnated in the one or more plastic polymers until opening. The scented film 128 is preferably thin and flexible, such as equal to or less than 1 mm, so that it does not significantly alter the elastic properties of the inner cuff 124. The scented film 128 is preferably harmless to the human body and resistant to degradation and fluids. The scented film 128 may be affixed with an adhesive and/or with heat or by other means. Though a scent embedded plastic polymer film is described herein, any other type of scented material may be implemented that includes a slowly evaporating scent detectable by a scent detector.

The scented film 128 may be affixed to an anterior portion of the inner cuff 124 as shown, or may alternatively be positioned on an anterior portion of the outer bladder 122, providing the scented film 128 is below the seal created between the cuff assembly 120 and the tracheal wall. In another example, the scented film 128 may be positioned on a distal end 126 of the tracheostomy tube 100, preferably near or adjacent to the cuff assembly 120. The scented film 128 is preferably not positioned near the distal opening 138 of the airway tube 100 where it may be unnecessarily exposed to inhaling and exhaling air, thereby possibly evaporating the scent from the film 128 too quickly. By placing the scented film 128 further from the air flow, such as on the posterior side of the cuff assembly 120, or adjacent to the cuff assembly 120 or just distal to the cuff assembly 120, the scent on the scented film 128 may persist for a longer period.

To detect an air leak, an air intake opening 130 is formed in the outer wall of the airway tube 100 on a proximal side of the cuff assembly 120, e.g., above the seal with the tracheal wall. The air intake opening 130 fluidly connects supracuff air in the trachea to a suction channel 136 (seen in FIGS. 2 and 3). A stopper 140 is positioned in the suction channel 136 distally from the opening 310 to prevent air from flowing into the suction channel 136 from a distal side of the cuff assembly 120. In another embodiment, the suction channel 136 ends at the air intake opening 130. A proximal end of the suction channel 136 attaches to air tubing 134 at the hub 110. An air pump fluidly attaches to an opposing end of the air tubing 134 such that the air pump is fluidly coupled to the air intake opening 130. The air tubing 134 or air pump further includes a valve that fluidly couples a scent detector to supracuff air flowing through the air tubing 134.

When the tracheostomy tube 100 is positioned in a patient and the cuff assembly 120 is inflated, an airtight seal should be formed between the cuff assembly 120 and the tracheal wall to prevent fluids and/or secretions from leaking into the trachea. When an airtight seal is not formed, air flow occurs from the scented film 128, through the seal, and into the air intake opening 130. The scented air then flows through the suction channel 136 to the air tubing 134 and to the scent detector. The scent detector may thus detect the scent and generate an alert that the seal is compromised, as described in more detail herein.

Figure 4A:
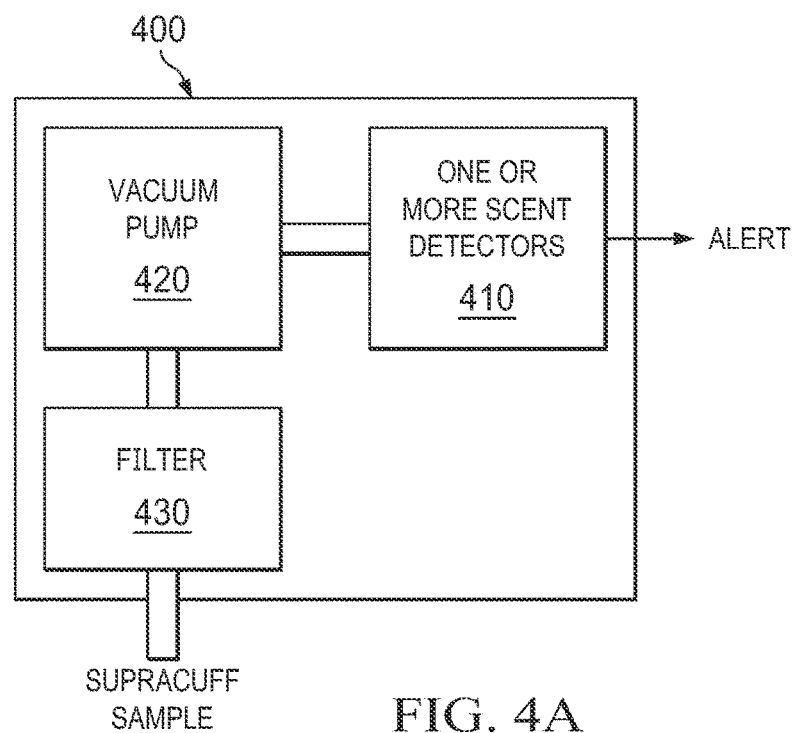
FIG. 4A illustrates a schematic block diagram of an embodiment of a scent detector system.

FIG. 4A illustrates a schematic block diagram of an embodiment of a scent detector system 400. The system 400 includes one or more scent detectors 410 and a vacuum pump 420. In one embodiment, the scent detector 410 is an electronic device that includes at least one receptor and at least one transducer. The receptor includes a compound designed to react with the chemicals in a predetermined scent in the scented film 128. The transducer then measures the chemical reaction to the predetermined scent. The chemical reaction may increase or decrease an impedance of the receptor. For example, when a polymer in the transducer contacts the predetermined scent, it expands, thereby changing its resistance. This change in resistance of the polymer is measured, and from that measurement, the presence of the predetermined scent is ascertained.

The vacuum pump 420 in the scent detector system acts as a low pressure vacuum to suction the supracuff air from the trachea. The vacuum pump 420 or air tubing 134 includes a valve and port to provide a sample of the supracuff area to the scent detector. Prior to the next test, the supracuff air in the trachea needs to be circulated and replaced to determine whether the scented air is still leaking from the tracheal wall seal. Otherwise, after the seal is improved and becomes airtight, the air pump may provide scented air remaining in the trachea from the previous test to the scent detector 410. The scent detector 410 would then detect the scent and generate an alert even though the seal is now airtight. To prevent this repeated sampling of the same air, the vacuum pump 420 suctions air from the trachea for a predetermined period of time. This period of suctioning removes the previously sampled air from the trachea and helps to draw a new batch of air into the trachea. After the predetermined period of suction, the air vacuum 420 provides a sample of air to the scent detector 410 where it is tested for the presence of the predetermined scent. When the scent detector 410 detects the predetermined scent, it then generates an alert. For example, the alert may include an audible alarm and/or a visible alert on a display, etc.

A filter 430 may also be implemented to filter the air sample from the suction channel 136 and/or tubing 134. The air sample may include secretions and other fluids that accumulate in the supracuff region, especially on the proximal side of the cuff assembly 120. So the air sample in the suction channel 136 and tubing 134 may also include such fluid. The filter 430 is configured to remove secretions or other fluids in the air sample with little to no removal of any predetermined scent in the air sample. In an embodiment, the suction of air and secretions from the supracuff region and filtering may occur at periodic intervals even when scent detection testing is not being performed. This periodic suction of the fluids in the supracuff region helps to prevent the accumulation of secretions that may cause leakage into the lungs.

Figure 4B:
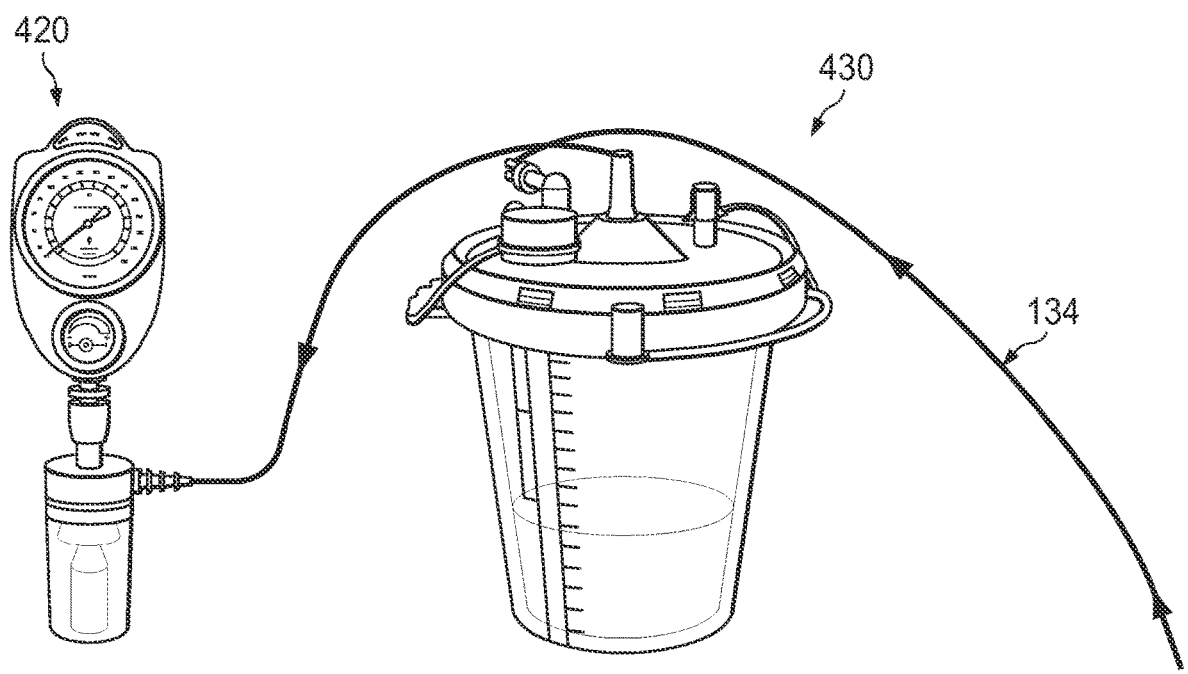
FIG. 4B illustrates a perspective view of an embodiment of a filter and vacuum pump in the scent detector system.

FIG. 4B illustrates a perspective view of an embodiment of the filter 430 and vacuum pump 420. In this example, the filter 430 is a liquid collection canister coupled to the suction channel 136 through the tubing 134. The supracuff air with secretions or other fluid enter the collection canister and liquids fall to a bottom of the canister due to their heavier weight. The air and any scent remain on the top of the canister. The suction vacuum siphons the air sample from the top of the canister and exposes the air sample to the scent detector. The collection canister may be equipped with overflow cut-off valves to prevent spillage.

Though a liquid collection canister is described herein, other types of air filters may be implemented. For example, coalescing filters may be implemented that use a filter media to remove droplets and other particulates from the air. In other examples, a mist eliminator or vapor removal filter provide alternatives to a coalescing filter.

In an embodiment, a syringe or vacuum may also attach to the tubing 134 to remove the secretions or other fluids that accumulate on the proximal side of the cuff assembly 120 when air testing is not being performed. The suction of secretions may occur at periodic intervals and may be competed manually or automatically.

Though a tracheostomy tube 100 is described herein, the cuff assembly 120 may be implemented in conjunction with any suitable medical device, including, but not limited to, an endotracheal tube or other airway tube, a catheter, a stent, and/or a feeding tube.

Embodiments of the Pressure Regulation System

Figure 5:
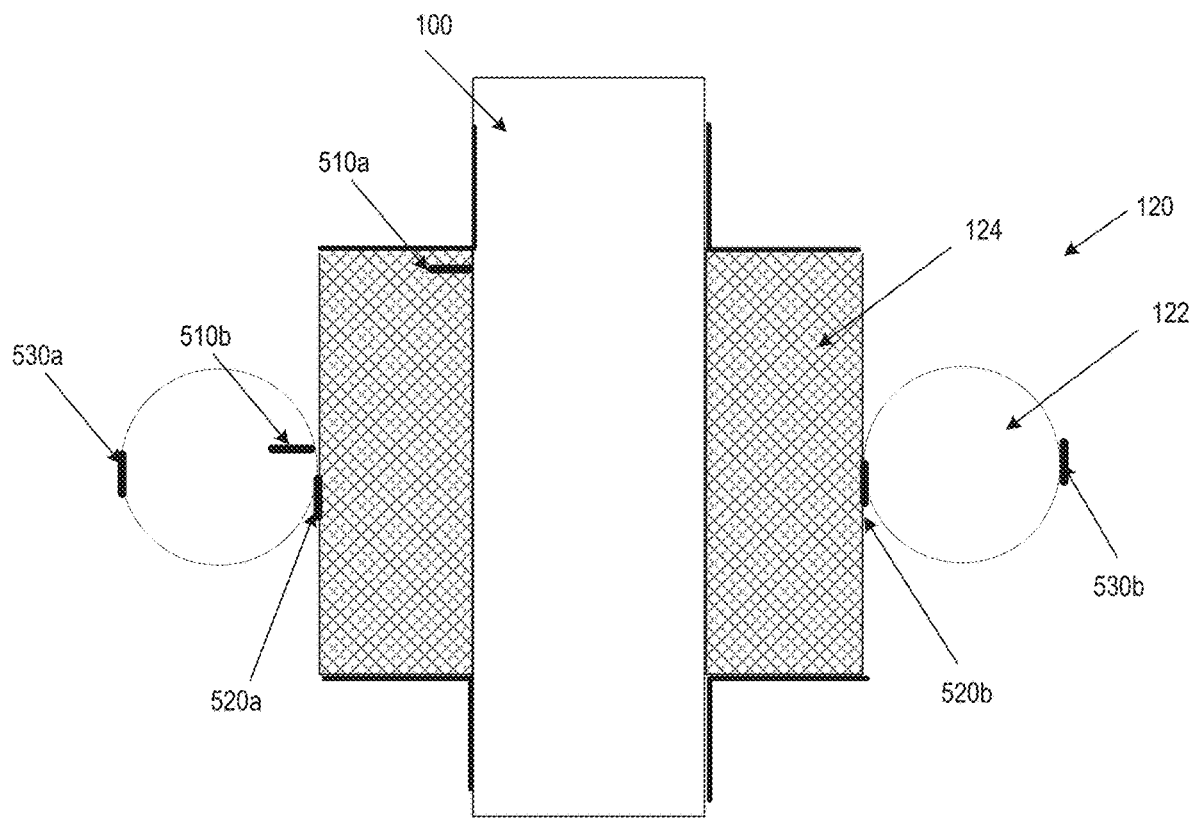
FIG. 5 illustrates a schematic block diagram of an embodiment of pressure sensors for a dual cuff assembly in an airway tube.

FIG. 5 illustrates a schematic block diagram of an embodiment of pressure sensors for an airway tube 100 (e.g., a tracheostomy tube, endotracheal tube, or other airway tube) including the cuff assembly 120. In an embodiment, the cuff assembly 120 includes at least one intracuff pressure sensor 510a associated with the inner cuff 124 and at least one intracuff pressure sensor 510b associated with the outer bladder 122. The intracuff pressure sensor 510a is positioned within the inner cuff 124 and is configured to measure an air pressure in the inner cuff 124. Additionally or alternatively, a pressure sensor (not shown) may be positioned at the proximal end of the inflation line 106a, e.g. as part of a pilot balloon, to measure the air pressure inside the inner cuff 124. The intracuff pressure sensor 510b is positioned inside the outer bladder 122 and is configured to measure an air pressure in the outer bladder 122. Additionally or alternatively, a pressure sensor (not shown) may be positioned at the proximal end of the inflation line 106b, e.g. at a pilot balloon, to measure the air pressure inside the outer bladder 122.

In an embodiment, one or more pressure sensors 530a-b may be positioned on an outer surface of the outer bladder 122 to measure a pressure or force that the cuff assembly 120 applies to the tracheal wall (the "tracheal pressure"). However, these sensor 530a-b may cause harm to the tracheal wall when pressed against it. So alternatively, or in addition to, one or more intercuff pressure sensors 520a-b may be positioned between the outer bladder 122 and the inner cuff 124 to measure the tracheal pressure. Since the force of the inner cuff 124 acts radially on the outer bladder 122, the intercuff pressure sensors 520a-b ultimately measure the force exerted by the cuff assembly 120 against the tracheal wall. As such, the intercuff pressure sensors 520a-b measure the tracheal pressure, e.g. the pressure exerted by the cuff assembly 120 against the tracheal wall. In one example, the tracheal wall pressure sensors 520a-b and 530a-b may include thin film pressure sensors with force sensitive resistors that change resistance based on an applied force. The pressure sensors 510*a-b* may include resistive or capacitive air pressure transducers. Additional pressure sensor devices may be positioned within the pilot balloons of the inflation lines 106*a-b* to measure the intracuff pressures or within the airway tube 100 or at the tip of the airway tube 100, to measure a pressure of the oxygenated air delivered to a patient.

The pressure sensors may each include a wireless transmitter to communicate pressure measurements to a pressure regulation system. For example, the wireless transmitter may include a wireless transmitter, such as a near field or radio frequency identification (RFID) transmitter or Internet of Things (IoT) cellular type transmitter. The pressure sensors may alternatively include wired transmitters to communicate pressure measurements.

The benefit and risks of the cuff assembly 120, more than the airway tube 100 itself, depends on maintaining a predetermined pressure range in the cuff assembly 120. For example, overinflation of the cuff assembly 120 may result in tracheal mucosal injury by causing ischemic damage and vocal cord nerve injury. The damage is due to the constant pressure exerted by the cuff that prevents blood flow to the mucosa of the trachea. This loss of blood flow may lead to tissue necrosis. In addition, damage may also arise due to the repeated abrasion from the cuff moving against the tracheal wall. When the cuff is underinflated and the tracheal seal is inadequate, the patient may not receive sufficient oxygen. Further, the patient is subjected to increased possibility of pneumonia from the aspiration of orogastric content. Thus, maintenance of the pressure of the cuff assembly 120 for an airway tube 100 is a critical component of patient care, vis-a-vis reduction of tracheal injury and prevention of ventilator-associated pneumonia (VAP).

Currently, several types of automated cuff pressure regulators are available. These current devices monitor an intracuff pressure within a single cuff. However, a close examination reveals a major flaw in this approach. The intracuff pressure does not reflect the precise pressure applied to the tracheal wall but only the air pressure within the inflated cuff. Ultimately, it is the tracheal wall pressure that determines both the risks and benefits of the cuff. Thus, there is a need for an improved system and method to monitor and regulate the cuff pressure.

Figure 6:
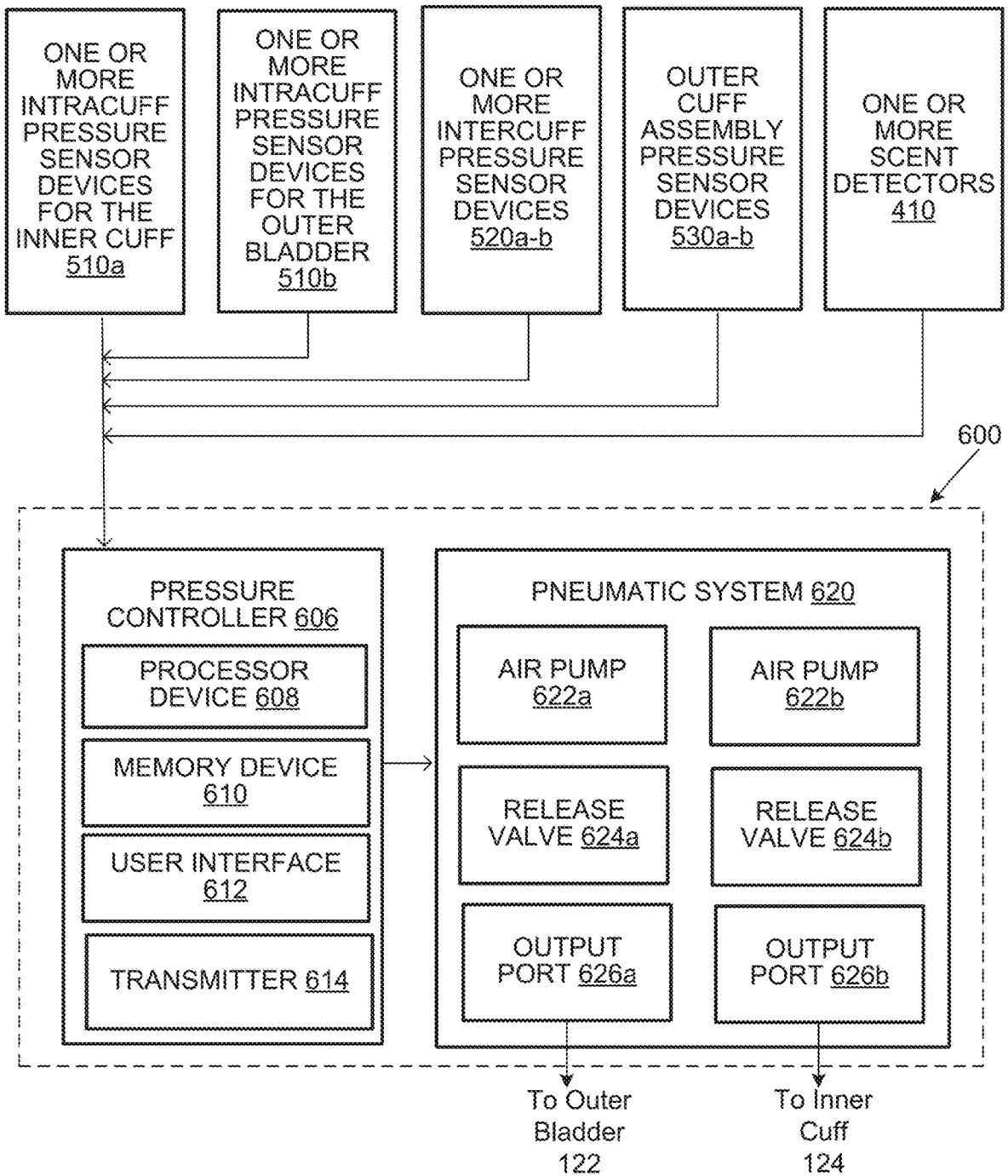
FIG. 6 illustrates a schematic block diagram of an exemplary embodiment of a pressure regulator and control system for a cuff assembly.

FIG. 6 illustrates a schematic block diagram of an exemplary embodiment of a pressure regulator and control system ("regulator system") 600 for the cuff assembly 120. The regulator system 600 fluidly communicates with and inflates and adjusts the pressure within the cuff assembly 120, e.g. when the airway tube 100 is implanted into the patient's trachea, using a measurement of the tracheal wall pressure and leak detection. The regulator system 600 includes a pressure controller 606 and pneumatic system 620. The pressure controller 606 includes a processor device 608 and a memory device 610. The memory device 610 includes one or more non-transitory processor readable memories that store instructions which when executed by the processor device 608 or other components of the regulator system 600, causes the regulator system 600 to perform one or more functions described herein. The processor device 608 includes at least one processing circuit, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The memory device 610 includes a non-transitory memory device and may be an internal memory or an external memory, and may be a single memory device or a plurality of memory devices. The memory device 610 may be a read-only memory, random access memory, volatile memory, non-volatile memory, static memory, dynamic memory, flash memory, cache memory, and/or any non-transitory memory device that stores digital information.

The pressure controller 606 may be co-located with the pneumatic system 620 in a same physical device or located separately in a different device or encasement. The pressure controller 606 further includes a user interface 612. The user interface 612 generates user input and output (I/O) and includes one or more of a display, keyboard, touch screen, mouse, touchpad, gauge, switch, or other I/O device.

In use, pressure settings are determined for the cuff assembly 120. The pressure controller 606 may use default pressure settings or pressure settings received from a user. Different pressure settings are used for the inner cuff 124 and the outer bladder 122. For example, the pressure setting for the inner cuff may be a pressure (plus or minus 2 cm $H_2O$) within the range of 10 cm $H_2O$ to 20 cm $H_2O$. In contrast, the pressure setting for the outer inflating bladder may be a pressure (plus or minus 2 cm $H_2O$) within the range of 50 cm $H_2O$ to 150 cm $H_2O$. The inner cuff 124 thus operates in a pressure range that is less than the operational pressure range of the outer bladder 122. The pressure controller 606 further determines a frequency of measuring and adjusting the pressure of the cuff assembly 120, e.g. either through a user input or default setting.

The pneumatic system 620 has a first pneumatic pathway for the outer bladder 122 that includes, e.g., a first air pump 622*a* and release valve 624*a* that fluidly couples with the outer bladder 122 through inflation line 106*b*. The pneumatic system 620 further includes a different, second pneumatic pathway for the inner cuff 124 that includes a second air pump 622*b* and release valve 624*b* that fluidly couples with the inner cuff 124 through, e.g., inflation line 106*a*. Though two air pumps 622*a*, 622*b* are described herein, a single air pump may supply the pressurized air to the inner cuff 124 and the outer bladder 122, e.g. using a valve or switch between the two fluid pathways. The pneumatic system 620 thus includes separate pneumatic pathways to fluidly increase or decrease the pressure in the inner cuff 124 and the outer bladder 122 independently and separately.

In operation, the pressure controller 606 receives pressure measurements from one or more pressure sensor devices to regulate the pressure of the cuff assembly 120. For example, the one or more pressure sensor devices may include one or more intracuff pressure sensor devices 510*a-b* located within the inflated inner cuff 124 and outer bladder 122 and/or in the pilot balloons of the inflation lines 106*a-b* to the cuff assembly 120. For example, the intracuff pressure sensor devices 510*a-b* measure the internal air pressures of the inner cuff 124 and the outer bladder 122 and communicate the measurements to the pressure controller 606. In addition, one or more intercuff pressure sensor devices 520*a-b* measure a tracheal wall pressure. One or more outer cuff assembly pressure sensor devices 530*a-b* may be positioned on an outer surface of the outer bladder 106 to further measure the tracheal wall pressure. The pressure controller 606 may also receive input from the one or more scent detectors 410. Additional pressure sensor devices may also be implemented. The pressure sensor devices generate and communicate pressure measurements to the pressure controller 606, e.g. either through a wired lead and/or a wireless transmitter 614.

The regulator system 600 includes a pressure feedback loop wherein the pressure controller 606 controls the pneumatic system 620 to adjust the pressures for both the inner cuff 124 and the outer bladder 122 responsive to the pressure measurements and/or the scent detectors. The pressures of the inner cuff 124 and the outer bladder 122 are monitored and controlled separately. The pressure controller 606 signals the pneumatic system 620 to add or release air to the outer bladder 122 and/or the inner cuff 124. For example, to adjust the pressure in the outer bladder 122, the pressure controller 606 may signal the air pump 622a to add air to the outer bladder 122 or signal the release valve 624a to release air from the outer bladder 122. In another example, to adjust the pressure in the inner cuff 124, the pressure controller 606 may signal the air pump 622b to add air to the inner cuff 124 or signal the release valve 624b to release air from the inner cuff 124.

The regulator system 600 monitors the pressure measurements from the pressure sensors and alerts from the scent detectors and adjusts the pressures in the cuff assembly 120 automatically in response thereto. The pressure controller 606 may monitor and adjust the pressure of the cuff assembly 120 continuously or may monitor and adjust the pressure at predetermined intervals. The regulator system 600 may further include visible and/or audible alarms in the event of unsafe pressure measurements.

Figure 7:
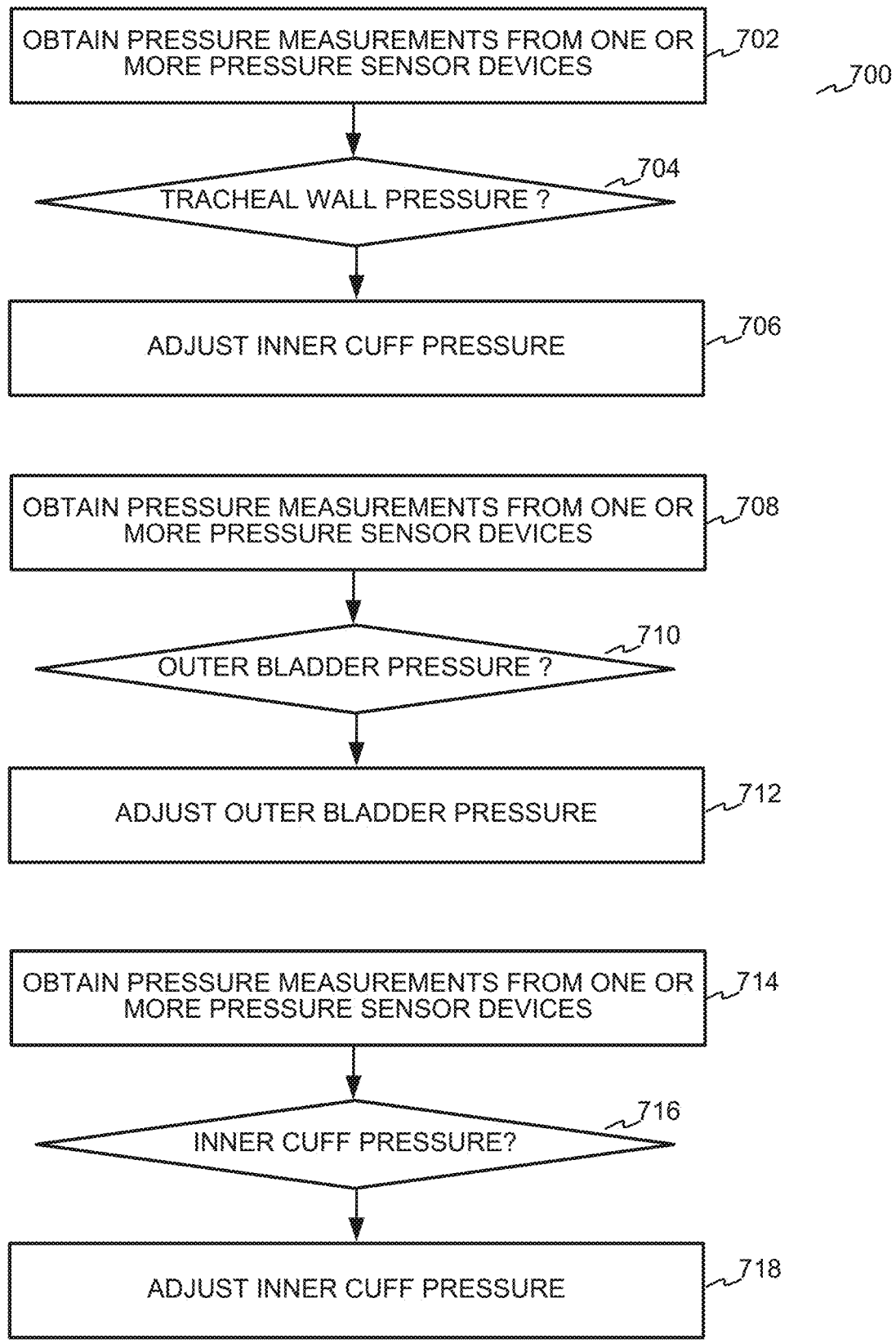
FIG. 7 illustrates a flow diagram of an embodiment of one or more methods for monitoring and controlling the pressure of a cuff assembly by the regulator system.

FIG. 7 illustrates a flow chart of an embodiment of one or more methods 700 for monitoring and controlling the pressure of the cuff assembly 120, e.g. by the regulator system 600. At step 702, one or more pressure measurements relating to the tracheal wall pressure are obtained by the regulator system 600 from one or more pressure sensor devices. Using these pressure measurements, the regulator system 600 determines whether the tracheal pressure, e.g. the pressure exerted by the cuff assembly 120 on the tracheal wall, is within a predetermined pressure range at step 704. The pressure measurements may be from the one or more intercuff pressure sensor devices 520a-b between the inner cuff 124 and the outer bladder 122 and/or from one or more pressure sensors 530a-b located on an outer surface of the outer bladder 122. When the tracheal pressure exceeds a predetermined pressure range, the regulator system 600 decreases at least the pressure in the inner cuff 124 at Step 706. For example, the regulator system 600 may control the release valve 624b to release air from the inner cuff 124. Since the tracheal mucosal blood flow may be compromised at applied pressures above 30 cm $H_2O$ (22 mm Hg), when the measured tracheal pressure exceeds 30 cm $H_2O$ (22 mmHg), then the regulator system 600 may decrease at least the pressure of the inner cuff 124.

When the tracheal pressure is less than a predetermined pressure range, the regulator system 600 increases at least the pressure in the inner cuff 124 at step 706. For example, the regulator system 600 may control the air pump 622b to pump air into the inner cuff 124. In addition, the pressure of the outer bladder 122 may also be adjusted. These steps may be performed at preset intervals or continuously.

At step 708, one or more pressure measurements relating to the outer bladder pressure are obtained by the regulator system 600 from one or more pressure sensor devices. Using these pressure measurements, the regulator system 600 determines whether the pressure of the outer bladder 122 is within a predetermined pressure range at step 710. For example, the pressure measurements may be from one or more pressure sensor devices 510b located within the outer bladder 122 or a pilot balloon for the outer bladder 122 or the inflation line 106b for the outer bladder 122. When the outer bladder 122 pressure is less than or more than the predetermined pressure range, the regulator system 600 increases or decreases the pressure in the outer bladder 122 at Step 712. For example, the regulator system 600 may control the air pump 622a to pump air into the outer bladder 122 when its pressure is below the predetermined pressure range or control the release valve 624a to release air from the outer bladder 122 when its pressure is above the predetermined pressure range. The outer bladder 122 may have a predetermined pressure range of 50 cm $H_2O$ to 150 cm $H_2O$.

At step 714, one or more pressure measurements relating to the pressure of the inner cuff 124 are obtained by the regulator system 600 from one or more pressure sensor devices. Using these pressure measurements, the regulator system 600 determines whether the pressure of the inner cuff 124 is within a predetermined pressure range at step 716. For example, the pressure measurements may be from one or more pressure sensor devices 510a located within the inner cuff 124 or at a pilot balloon for the inner cuff 124 or the inflation line 106a for the inner cuff 124. When the inner cuff pressure is less than or more than the predetermined pressure range, the regulator system 600 may increases or decrease the pressure in the inner cuff 124 at Step 718. For example, the regulator system 600 may control the air pump 622b to pump air into the inner cuff 124 when its pressure is below the predetermined pressure range or control the release valve 624b to release air from the inner cuff 124 when its pressure is above the predetermined pressure range. In one example, the predetermined pressure range may be 10 cm $H_2O$ to 20 cm $H_2O$.

The pressure of the inner cuff 124 and the outer cuff bladder 122 of the cuff assembly 120 are thus controlled separately using separate pneumatic pathways, e.g., separate air pumps 622 and/or release valves 624 and separate inflation lines 106a-b. The pressure of the more inelastic outer bladder 122 is maintained at a higher pressure than the pressure of the more elastic inner cuff 124. The pressure controller 602 may thus independently adjust a pressure of the inner cuff 124 or the outer bladder 122 to adjust the tracheal pressure.

Figure 8A:
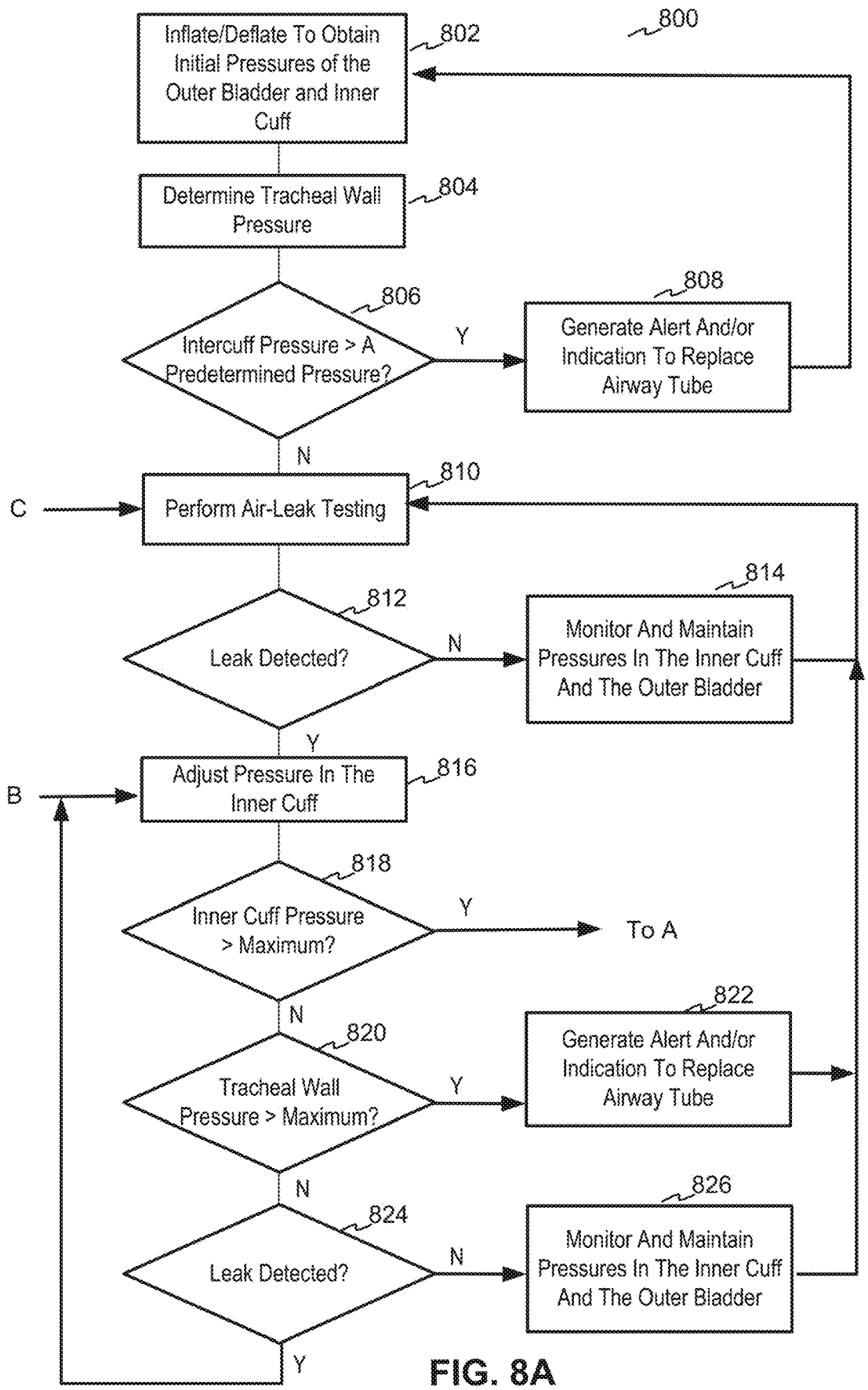
FIGS. 8A and 8B illustrate a flow diagram of an embodiment of a method for determining an operating pressure for a cuff assembly.
Figure 8B:
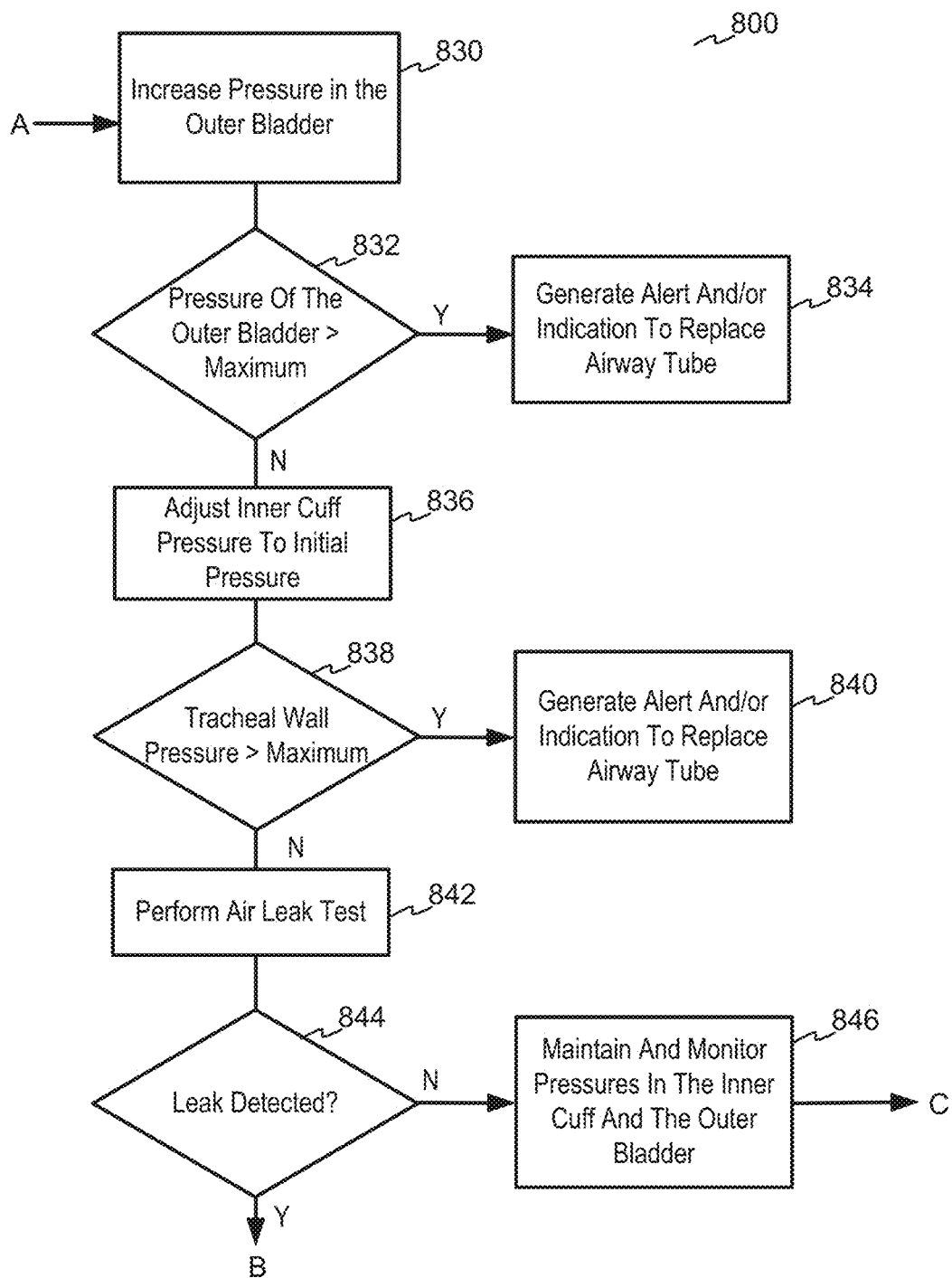

FIGS. 8A-B illustrate a schematic block diagram of an embodiment of a method 800 for determining an operating pressure for the cuff assembly 120. After implantation, a cuff-bladder pressure adjusting process may be performed to determine an operating pressure. The process 800 may also be performed, in whole or in part, after inflation in response to a leak detection, an out-of-range pressure measurement from either the inner cuff 124, the outer bladder 122, or the tracheal wall pressure (e.g., from the intercuff sensors 520a-b or outer cuff assembly sensors 530a-b), or in response to a manual request.

The process 800 begins with the pressure regulator system 600 inflating or deflating the inner cuff 124 and the outer bladder 122 to respective initial pressure levels at 802. For example, the initial pressure level for the inner cuff 124 may include a pressure range of 8-12 cm $H_2O$, or approximately 10 cm $H_2O$. The initial pressure level for the outer bladder 122 may include a pressure range of 35-45 cm $H_2O$, or approximately 40 cm $H_2O$. The initial pressure levels may be set by default or may be input by an operator through a user interface 612.

After the inner cuff 124 and outer bladder 122 are at their respective initial pressure levels, the tracheal wall pressure is obtained at 804. The pressure regulator 600 may determine the tracheal wall pressure from an average, mean or maximum of the measurements from the intercuff pressure sensors 520a-b and/or pressure sensor devices 530a-b on the outer surface of the cuff assembly 120. When the tracheal wall pressure is greater than a predetermined maximum tracheal pressure at 806, an alert is generated at 808. The alert may indicate that the maximum tracheal pressure is exceeded and/or may indicate to replace the current airway tube (such as an endotracheal or tracheotomy tube), e.g., with an airway tube having a greater outer diameter. When the airway tube is replaced, the process 800 begins again at 802.

When the tracheal wall pressure is under the predetermined maximum tracheal pressure at 806, an air leak test is performed at 810. The air leak test includes obtaining an air sample from a supracuff area of the trachea. The air-evacuating system (such as the opening 130, suction channel 136, and airway tubing 134) of the airway 100 is connected to a low-pressure vacuum pump 420 to provide good circulation in the supracuff area. The supracuff air is sampled for the presence of the one or more predetermined scents. When no air leak is detected at 812, it indicates that the cuff assembly 120 has a good seal with the tracheal wall. The pressures of the cuff assembly 120 are then maintained and monitored at 814. The air-leak testing may be repeated periodically or upon command to ensure the cuff assembly 120 maintains a good seal with the tracheal wall.

When an air leak is detected at 812, this indicates that the cuff assembly 120 does not have a good seal against the tracheal wall. To obtain a better seal, the pressure in the inner cuff 124 is adjusted at 816. For example, the pressure in the inner cuff 124 may be increased in increments of 1-2 cm $H_2O$. After an increment increase in pressure of the inner cuff 124, it is determined at 818 whether the pressure in the inner cuff is greater than 25 $H_2O$, e.g. the maximum inner cuff pressure. When it is not, it is determined whether the tracheal wall pressure is more than the maximum tracheal wall pressure at 820. When the tracheal wall pressure exceeds the maximum tracheal wall pressure at 820, then an alert is generated at 822. The alert may indicate that the maximum tracheal pressure is exceeded and/or may indicate to replace the current airway tube (such as an endotracheal or tracheotomy tube), e.g., with an airway tube having a greater outer diameter. When the airway tube 100 is replaced, the process 800 begins again at 802.

When the tracheal wall pressure is below the maximum tracheal wall pressure at 820, another air leak test is performed at 824. These steps of incrementing the pressure in the inner cuff 124 and performing an air leak test may be repeated until the pressure in the inner cuff 124 is greater than the maximum inner cuff pressure (e.g., 25 cm $H_2O$) or the tracheal wall pressure exceeds the maximum tracheal pressure (e.g., 25 cm $H_2O$). When no leak is detected at 824, then the pressure of the cuff assembly 120 is maintained and monitored at 826. The air-leak testing may be repeated periodically or upon command to ensure the cuff assembly 120 maintains a good seal with the tracheal wall.

When a leak is still detected at 824 and the incremented pressure of the inner cuff 124 exceeds the maximum inner cuff pressure at 818, then the process proceeds to step 830 of FIG. 8B, as shown by the arrow A. At step 830, the pressure in the outer bladder 122 is adjusted. For example, the pressure in the outer bladder may be increased in increments of 2-3 cm $H_2O$. After an increment increase in pressure of the outer bladder 122, it is determined at 832 whether the pressure in the outer bladder 122 is greater than a maximum outer bladder pressure, e.g. 60 cm $H_2O$. When the outer bladder 122 is greater than a maximum outer bladder pressure at 832, then an alert is generated at 834. The alert may indicate that the maximum outer bladder pressure is exceeded with a leak detection and/or may indicate to replace the current airway tube (such as an endotracheal or tracheotomy tube), e.g., with an airway tube having a greater outer diameter. When the airway tube 100 is replaced, the process 800 begins again at 802.

When the pressure in the outer bladder 122 is not greater than a maximum outer bladder pressure at 832, the inner cuff pressure is adjusted to a lower pressure, such as the initial pressure of 10 cm $H_2O$ at 836. At 838, it is determined whether the tracheal wall pressure is more than the maximum tracheal wall pressure. When it is greater than the maximum tracheal wall pressure, then an alert is generated at 840. The alert may indicate that the maximum tracheal pressure is exceeded and/or may indicate to replace the current airway tube (such as an endotracheal or tracheotomy tube), e.g., with an airway tube having a greater outer diameter. When the airway tube 100 is replaced, the process 800 begins again at 802.

When the tracheal wall pressure is below the maximum pressure at 838, an air leak test is performed at 842. The air leak test determines whether a good seal has been formed at the new incremented pressure of the outer bladder 122 and the initial pressure of the inner cuff 124. When no leak is detected at 844, the pressures of the cuff assembly 120 are maintained and monitored at 846. The process continues to step 810 in FIG. 8A as shown by arrow C. Periodic air leak testing is performed to ensure the cuff assembly 120 maintains a good seal with the tracheal wall.

When a leak is detected at 844 at the new incremented pressure of the outer bladder 122 and the initial pressure of the inner cuff 124, then the process continues to step 816 in FIG. 8A as shown by arrow B. The initial pressure of the inner cuff 124 is then incremented until no leak is detected at 824 or a maximum inner cuff pressure is reached at 818. When the maximum inner cuff pressure is reached at 818, then the process again continues to 830 and the pressure in the outer bladder 122 is incremented to a higher pressure. The process 800 is completed when no air leak is detected at 824 or 844, the pressures of the inner cuff and the outer bladders are less than their respective maximums, and the tracheal wall pressure is less than a maximum.

In this process 800, the pressure in the inner cuff 124 is incremented first through its operating range while maintaining the initial pressure of the outer bladder. If a leak is still detected, the outer bladder pressure is incremented to a higher pressure, and the inner cuff is reset to its initial pressure and incremented through its operating range until a leak is not detected. Throughout the process 800, the tracheal wall pressure is not to exceed a maximum pressure, e.g. within a range of 20-25 cm $H_2O$. Should the tracheal wall pressure exceed the maximum pressure to achieve an air-tight cuff-bladder inflation, the size of the airway tube is adjusted, e.g., up-sized to a next size larger. When another airway tube is implanted in the patient, the entire process 800 is repeated to adjust the pressures in the cuff assembly 120. The cuff assembly 120 and the regulator system 600 thus provide for a process to determine and maintain an optimized operating pressure without leaks for the cuff assembly 120. This process helps to reduce micro-aspiration and infection of the lungs by obtaining and maintaining a good seal with the tracheal wall without unduly harming the tracheal wall.

Figure 9:
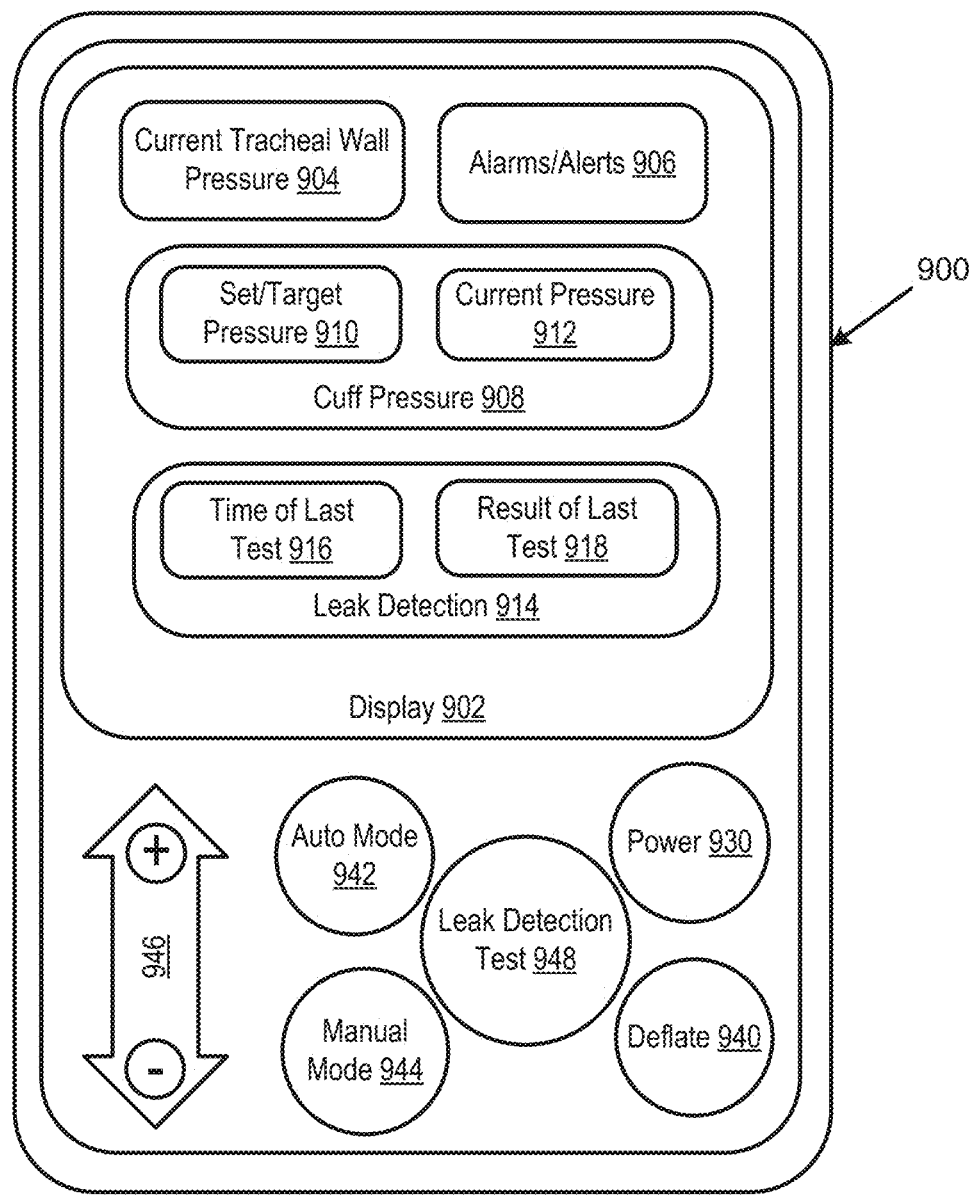
FIG. 9 illustrates a schematic block diagram of an embodiment of a user interface for the pressure regulator system.

FIG. 9 illustrates a schematic block diagram of an embodiment of a user interface 900 for the pressure regulator system 600. The user interface 900 receives settings and commands from a user. In one example, the user interface 900 includes a display 902 that may be an interactive touch screen. The display 902 includes one or more icons or data displays, such as a display of a current tracheal wall pressure 904 and alarms/alerts 906. The display 902 further includes a display of the cuff pressure 908, such as the set or target pressure 910 and current pressure 912 of the inner cuff 124 and outer bladder 122. The display 902 may also include a display of the leak detection 914, such as a time of the last test 916 and result of the last test 918. Additional and/or alternate data may also be presented in the display 902.

The user interface 900 further includes one or more user input devices, such as knob controllers, push buttons, touch pads, switches, etc. to receive one or more commands from a user. Alternatively, the display 900 may include an interactive touch screen that displays one or more icons to receive the user commands. For example, the user interface 900 includes a power button/icon 930 to initiate power up of the pressure regulator 600. A deflate button/icon 940 initiates deflation of the cuff assembly 120, e.g. such as for removal of the airway tube 100 from a patient.

An auto mode button/icon 942 may be activated to initiate auto mode. In the auto mode, the pressure regulator 600 automatically inflates the cuff assembly to default settings and performs one or more processes described in FIGS. 8A-B to determine an operating pressure without detected leaks for the cuff assembly 120. After inflation, in an auto mode, the pressure regulator 600 performs automatic cuff pressure measurements and pressure adjustments of the cuff assembly 120 in addition to leak detection tests at predetermined intervals. The predetermined interval may have a default of 30 minutes with a manual setting between 5 minutes to 4 hours.

The user interface 900 further includes a manual mode button/icon 944 to initiate a manual mode. In the manual mode, default settings may be input such as default pressure settings for the cuff assembly 120, maximum pressure settings for the cuff assembly and/or the tracheal wall pressure, interval between leak detection tests, interval between pressure measurements, etc. In the manual mode, an "initial pressure set" button/icon may be manually activated to inflate the cuff assembly 120 to default settings and perform one or more processes described in FIGS. 8A-B to determine an optimized operating pressure without leaks for the cuff assembly 120. After inflation, a cuff pressure measurement check may be manually activated including a manual pressure adjustment using the arrow key 946. A leak detection test may be initiated manually by activating the corresponding icon/button 948. The user interface 900 may include other commands and/or data for operation of the pressure regulator 600.

Figure 10:
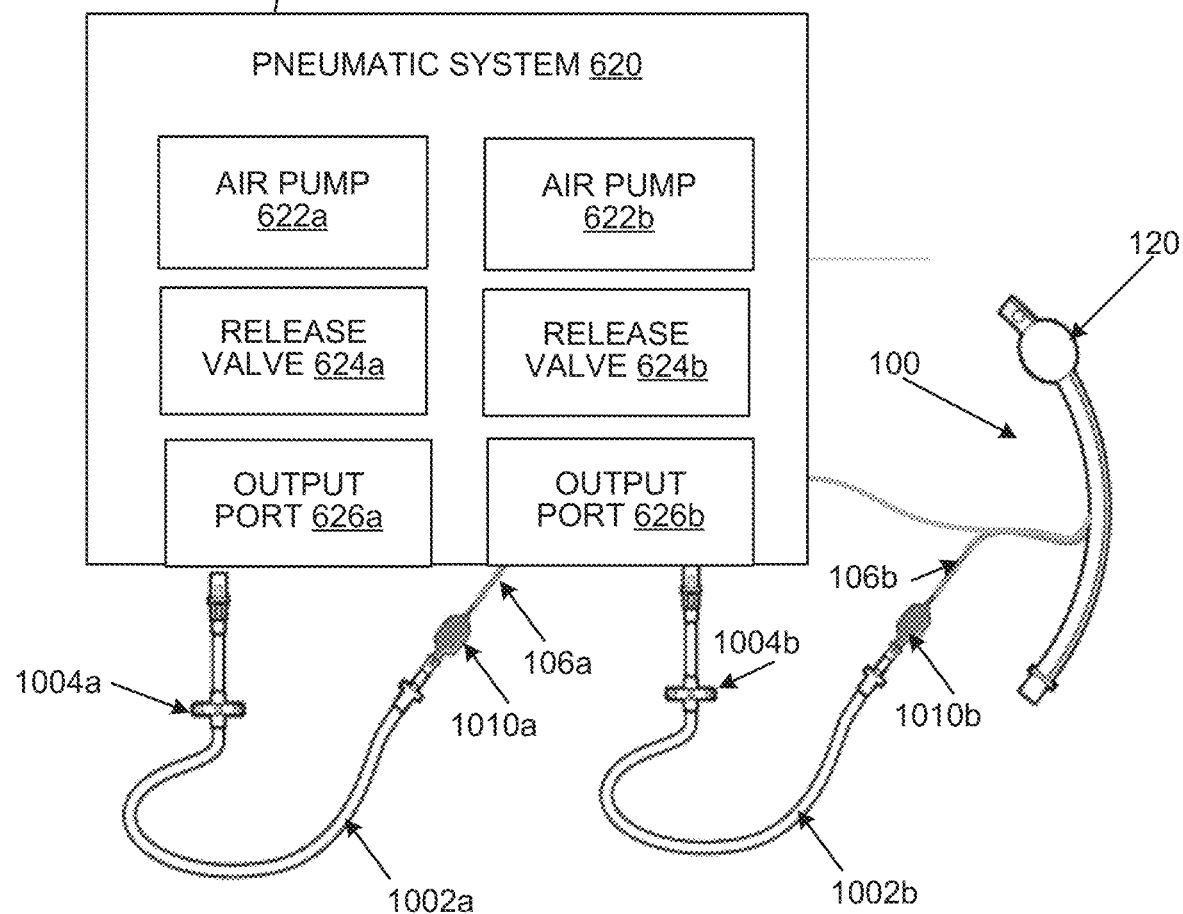
FIG. 10 illustrates a schematic block diagram of an embodiment of the pressure regulator system.

FIG. 10 illustrates a schematic block diagram of an embodiment of the pressure regulator system 600. In one example, the user interface 900 is included in a control module 1000 that may also include the pressure controller 606. The pneumatic system 620 may be in a separate encasement as shown or included with the control module 1000. When in separate encasements, the pneumatic system 620 and the pressure controller 606 may communicate using wired or wireless transmitters.

The pneumatic system 620 includes the first output port 626a coupled to extension tubing 1002a for inflating the outer bladder 122 of the cuff assembly 120. The extension tubing 1002a may include an air filter 1004a to filter any contaminants and attaches to the inflation line 106a of the airway tube 100. The inflation line 106a may include a pilot balloon 1010a that serves as an indication of the air pressure in the outer bladder 122. The pneumatic system 620 includes the second output port 626b coupled to extension tubing 1002b for inflating the inner cuff 124 of the cuff assembly 120. The extension tubing 1002b may include an air filter 1004b to filter any contaminants and attaches to the inflation line 106b of the airway tube 100. The inflation line 106b may also include a pilot balloon 1010b that serves as an indication of the air pressure is in the inner cuff 124. In addition to the inflation lines 106a-b, additional manual inflation lines may be connected to the cuff assembly 120 for manually inflating the inner cuff 124 and outer bladder 122, e.g., using a parenteral syringe.

Figure 11:
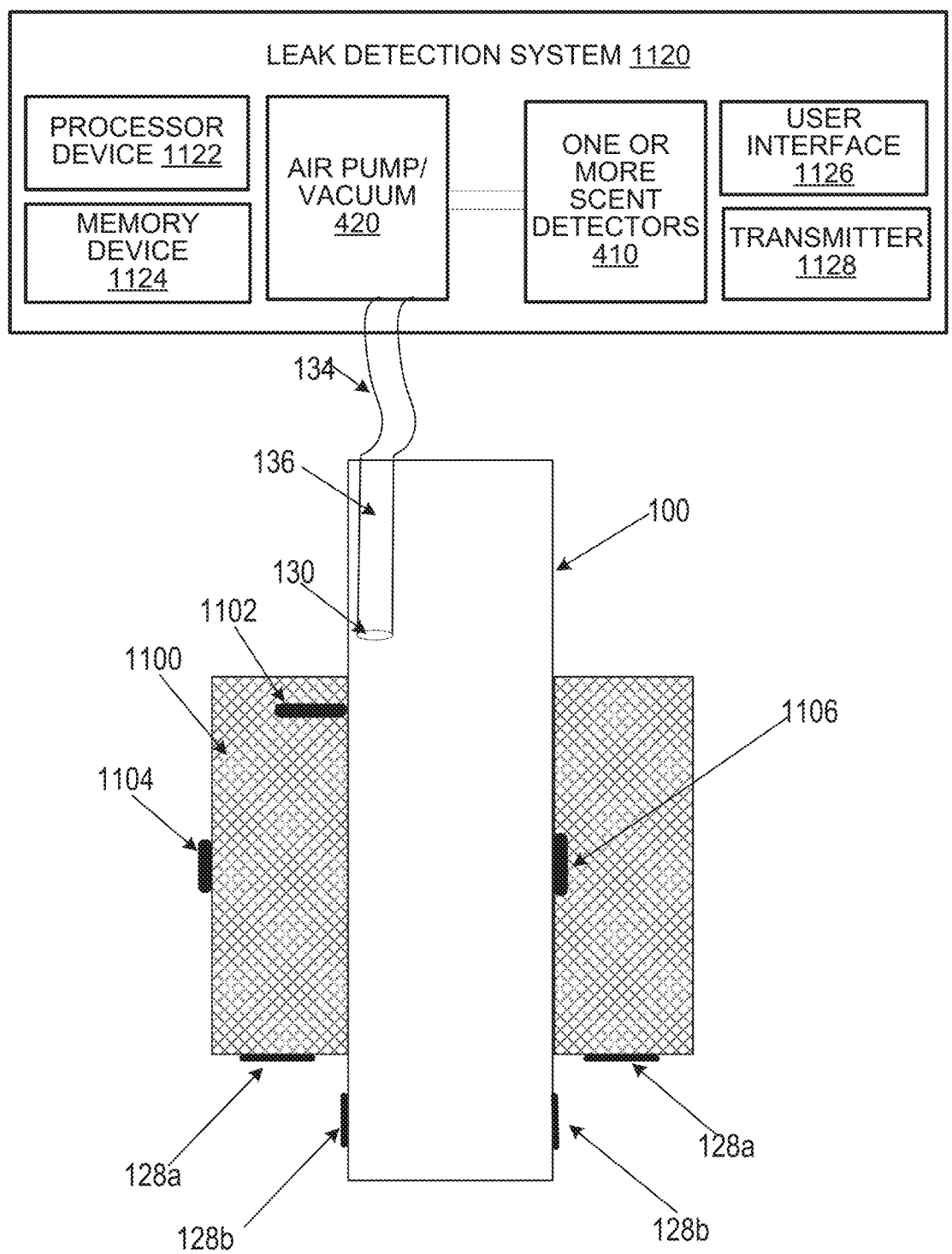
FIG. 11 illustrates a schematic block diagram of an embodiment of the leak detection and pressure regulation system for a single cuff assembly.

Though the cuff assembly 120 is described as including an inner cuff 124 and outer bladder 122, the pressure regulation system 600 and methods described herein may also be implemented with a single inflatable cuff. FIG. 11 illustrates a schematic block diagram of an embodiment of the leak detection and pressure regulation system for a single cuff assembly. In this example, the cuff assembly includes a single inflated cuff 1100 encircling the airway tube 100. One or more intracuff sensors 1102 are positioned to measure an air pressure within the cuff 1100, e.g. positioned within the cuff 1100 and/or in a pilot balloon connected to an inflation line for the cuff 1100. One or more pressure sensors 1104 may be coupled externally to the cuff 1100 to measure a force applied to the tracheal wall. The tracheal wall pressure may also be measured using one or more pressure sensors 1106 positioned between the cuff 1100 and the airway tube 100. The pressure measurements may be transmitted periodically to the pressure controller 606 using wired or wireless transmitters in the pressure sensors 1102, 1104, 1106.

The airway tube 100 and cuff 1100 may also include the leak detection system 1120. The leak detection system 1120 includes one or more scented films 128 located on a distal side of the cuff 1100. The one or more scented films 128a may be located circumferentially around a distal side of the cuff 1100. Additionally or alternatively, one or more scented films 128b may be located circumferentially around the airway tube 100. The scented films 128a-b include an embedded scent detectable by the one or more scent detectors 410.

The airway tube 100 further includes an air intake opening 130 formed in the outer wall that fluidly connects to a suction channel 136. The suction channel 136 and opening 130 are preferably on a proximal side of the cuff assembly 120. Air tubing 134 attaches to a proximal end of the suction channel 136 and a vacuum pump 420 attaches to the air tubing 134. The vacuum pump 420 suctions air from the trachea through the opening 130. The vacuum pump 420 obtains an air sample for the one or more scent detectors 410. The scent detectors 410 communicate measurements to the pressure controller 606.

The pressure controller 606 may control the vacuum pump 420 and scent detectors 410 and/or a separate processor device 1122 with a memory device 1124 may control the leak detection system 1120. The memory device 1124 includes one or more non-transitory processor readable memories that store instructions which when executed by the processor device 1122 or other components of the leak detection system 1120, causes the leak detection system 1120 to perform one or more functions described herein. The leak detection system 1120 also includes a user interface 1126 and transmitter 1128.

Figure 12:
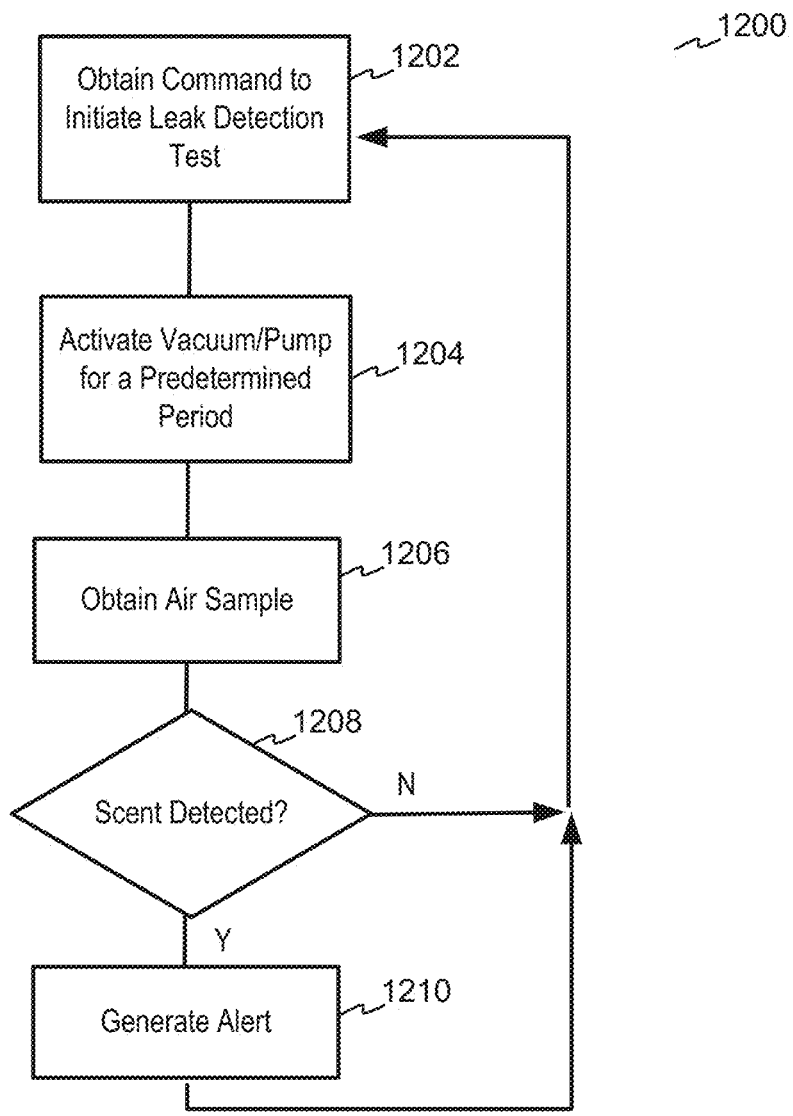
FIG. 12 illustrates a schematic flow diagram of an embodiment of a method for leak detection of a tracheal seal formed by a cuff assembly in an airway tube.

FIG. 12 illustrates a schematic flow diagram of an embodiment of a method 1200 for leak detection of a tracheal seal formed by a cuff assembly 120 in an airway tube 100. The cuff assembly 120 may include a single inflated cuff 1100 or dual cuffs 122, 124. The method 1200 may be performed by a separate leak detection system 1120 or by a pressure controller 606 that controls the cuff assembly 120. At 1202, a command is obtained to initiate a leak detection test. The command may be automatically generated at preset intervals or manually input.

The vacuum pump 420 is activated for a predetermined period at 1204 to obtain an air sample from the trachea proximal to the cuff assembly at 1206. The predetermined period is set such that the supracuff air in the trachea is circulated and refreshed between tests. The scent detectors 410 are exposed to the air sample and determine whether a scent is detected at 1208. When a scent is not detected at 1208, the leak detection system 1120 returns to step 1202 to wait for a command to perform another test. When a scent is detected at 1208, an alert is generated at 1210. The alert may be an audible alarm and/or a visual display. The pressure in the cuff assembly 120 may then be adjusted, and the leak detection process repeated.

The cuff assembly 120, pressure regulator system 600, and the leak detection system 1120 improve the protection and safety of intubated patients. The cuff assembly 120 and the pressure regulator system 600 maintain an improved seal with the tracheal wall that reduces leakage of secretions and infection of the lungs without unduly harming the tracheal wall. The automated pressure measurements and adjustments also helps save caregiver time. The leak detection system 1120 provides an early warning of a possible problem with the seal formed by the cuff assembly 120 against the tracheal wall. Intervention may then be provided earlier to help prevent leakage of secretions into the lungs. Additional or alternative advantages and improvements are possible in one or more of the embodiments described in the specification and/or the claims.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled," "coupled to," "connected to" and/or "connecting" or "interconnecting" includes direct connection or link between nodes/devices and/or indirect connection between nodes/devices via an intervening item. As may further be used herein, inferred connections (i.e., where one element is connected to another element by inference) includes direct and indirect connection between two items in the same manner as "connected to." As may be used herein, the terms "substantially" and "approximately" provides an industry-accepted tolerance for its corresponding term and/or relativity between items.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A medical device, comprising:
   an airway tube configured for implantation within a trachea;
   a cuff assembly implemented on a distal portion of the airway tube, wherein the cuff assembly includes at least one inflatable cuff;
   at least one scented material positioned on an inferior portion of the cuff assembly or on the airway tube distal from the cuff assembly; and
   at least one scent detector configured to detect a predetermined scent from the scented material in air, wherein the air is sampled from the trachea on a proximal side of the cuff assembly.

2. The medical device of claim 1, wherein the airway tube further includes:
   an air intake opening formed in an outer wall of the airway tube proximally from the cuff assembly; and
   a suction channel extending from the air intake opening to a proximal end of the airway tube.

3. The medical device of claim 2, further comprising:
   a vacuum pump fluidly coupled to the suction channel at the proximal end of the airway tube, wherein the vacuum pump suctions the air from the trachea through the air intake opening and suction channel; and
   a filter configured to remove fluids from the air prior to testing by the at least one scent detector.

4. The medical device of claim 1, further comprising:
   a pressure regulator system configured to adjust a pressure in the at least one inflatable cuff of the cuff assembly in response to the at least one scent detector.

5. The medical device of claim 4, wherein the pressure regulator system is configured to:
   determine the at least one scent detector has detected a leak around the cuff assembly, wherein the at least one scent detector includes a chemical and/or electronic sensor configured to detect the predetermined scent;
   generate an alert on a user interface, wherein the alert includes one or more of: an audible alert or a visual alert; and
   adjust the pressure in the at least one inflatable cuff of the cuff assembly in response to the detected leak.

6. The medical device of claim 5, further comprising:
   a first inflation lumen with a first distal end coupled to an interior of the at least one inflatable cuff and a second proximal end fluidly coupled to a first air pump and a first release valve to add or remove air from the at least one inflatable cuff.

7. The medical device of claim 4, further comprising:
   a pressure sensor device configured to measure a tracheal wall pressure exerted by the cuff assembly.

8. The medical device of claim 7, wherein the pressure regulator system is configured to:
   adjust the pressure in the at least one inflatable cuff of the cuff assembly in response to a detected leak based on the at least one scent detector and the tracheal wall pressure.

9. The medical device of claim 8, wherein the at least one inflatable cuff is an inner cuff positioned adjacent to the airway tube; and
   wherein the cuff assembly further includes an inflatable outer bladder positioned adjacent to an outer surface of the inner cuff.

10. The medical device of claim 9, wherein the pressure sensor device configured to measure the tracheal wall pressure is positioned between the inner cuff and the outer bladder.

11. The medical device of claim 9, wherein the inner cuff is configured to be inflated within a first pressure range and wherein the outer bladder is configured to be inflated within a second pressure range, wherein the first pressure range is less than the second pressure range.

12. The medical device of claim 1, wherein the at least one scented material comprises a scent-embedded polymer film, wherein the scent-embedded polymer film is not degradable, is water resistant, and does not alter an elasticity of the at least one inflatable cuff.

13. The medical device of claim 12, wherein the predetermined scent in the at least one inflatable cuff is released in detectable amounts over a period between two to three months.

14. A medical system, comprising:
   an airway tube configured for implantation within a trachea;
   a cuff assembly on a distal portion of the airway tube;
   at least one scented material positioned on a distal side of the cuff assembly or on a portion of the airway tube distal from the cuff assembly, wherein the at least one scented material includes at least one predetermined scent;
   an air intake opening formed in an outer wall of the airway tube proximally from the cuff assembly;
   a suction channel extending from the air intake opening to a proximal end of the airway tube; and
   at least one scent detector configured for detection of the at least one predetermined scent in supracuff air from the trachea.

15. The medical system of claim 14, wherein the at least one scent detector includes a chemical and/or electronic sensor configured for detection of the at least one predetermined scent in the supracuff air from the trachea.

16. The medical system of claim 14, wherein the medical system further includes:
   a user interface that emits an audible or visible alert when the at least one scent detector detects the at least one predetermined scent in the supracuff air.

17. The medical system of claim 14, wherein the medical system further includes:
   a pressure regulator system configured to adjust a pressure of the cuff assembly when the at least one scent detector detects the at least one predetermined scent in the supracuff air.

18. The medical system of claim 17, wherein the medical system further includes:
   a pressure sensor device configured to measure a tracheal wall pressure exerted by the cuff assembly; and
   wherein the pressure regulator system is further configured to adjust the pressure of the cuff assembly in response to the tracheal wall pressure.

19. A medical system, comprising:
   an airway tube configured for implantation within a trachea;
   a cuff assembly on a distal portion of the airway tube, wherein the cuff assembly includes an inner cuff positioned adjacent to the airway tube and an outer bladder positioned adjacent to the inner cuff;
   at least one scented material positioned on an inferior portion of the inner cuff or on a portion of the airway tube distal from the cuff assembly, wherein the at least one scented material includes at least one predetermined scent; and at least one scent detector configured to detect the at least one predetermined scent in supracuff air from the trachea.

20. The medical system of claim 19, further comprising:

a pressure regulator system configured to adjust a pressure of the inner cuff and/or the outer bladder in response to the at least one scent detector detecting the at least one predetermined scent.

21. The medical system of claim 19, wherein the at least one scent detector includes a chemical and/or electronic sensor.

\* \* \* \* \*